(12) United States Patent
Messmer et al.

(10) Patent No.: US 11,680,948 B2
(45) Date of Patent: Jun. 20, 2023

(54) DETECTION AND QUANTIFICATION OF NATALIZUMAB

(71) Applicant: ABREOS BIOSCIENCES, INC., San Diego, CA (US)

(72) Inventors: Bradley T. Messmer, San Diego, CA (US); Dina Uzri, San Diego, CA (US); Jessie-Farah Fecteau, San Diego, CA (US)

(73) Assignee: ABREOS BIOSCIENCES, INC., San Diego, CA (US)

( * ) Notice: Subject to any disclaimer, the term of this patent is extended or adjusted under 35 U.S.C. 154(b) by 1058 days.

(21) Appl. No.: 16/324,878

(22) PCT Filed: Aug. 11, 2017

(86) PCT No.: PCT/US2017/046499
§ 371 (c)(1),
(2) Date: Feb. 11, 2019

(87) PCT Pub. No.: WO2018/031887
PCT Pub. Date: Feb. 15, 2018

(65) Prior Publication Data
US 2021/0285959 A1    Sep. 16, 2021

Related U.S. Application Data

(60) Provisional application No. 62/374,217, filed on Aug. 12, 2016.

(51) Int. Cl.
*G01N 33/68* (2006.01)
(52) U.S. Cl.
CPC ............ *G01N 33/6854* (2013.01); *G01N 2333/70546* (2013.01)
(58) Field of Classification Search
CPC ..... G01N 33/6854; G01N 2333/70546; C07K 7/08
See application file for complete search history.

(56) References Cited

U.S. PATENT DOCUMENTS

| | | |
|---|---|---|
| 5,281,395 A | 1/1994 | Markart et al. |
| 5,413,764 A | 5/1995 | Haar |
| 5,567,594 A | 10/1996 | Calenoff |
| 5,877,028 A | 3/1999 | Chandler et al. |
| 5,885,577 A | 3/1999 | Alvarez |
| 6,146,589 A | 11/2000 | Chandler |
| 6,210,901 B1 | 4/2001 | Seidel et al. |
| 6,596,476 B1 * | 7/2003 | Lesniewski ........ G01N 33/5767 435/5 |
| 7,074,888 B1 | 7/2006 | Miller et al. |
| D579,459 S | 10/2008 | Tomizawa et al. |
| 8,193,002 B2 | 6/2012 | Guo et al. |
| 8,507,216 B2 | 8/2013 | Kuroda et al. |
| D701,875 S | 4/2014 | D'Amore et al. |
| D731,528 S | 6/2015 | Nagasawa et al. |
| D732,062 S | 6/2015 | Kwon |
| D750,113 S | 2/2016 | Kettner et al. |
| 9,250,233 B2 | 2/2016 | Kipps et al. |
| D757,040 S | 5/2016 | Zankowski et al. |
| 9,329,187 B2 | 5/2016 | Yin et al. |
| D766,936 S | 9/2016 | Pham et al. |
| D771,072 S | 11/2016 | Protzman et al. |
| D774,205 S | 12/2016 | Grace et al. |
| D780,188 S | 2/2017 | Xiao et al. |
| D797,761 S | 9/2017 | Tsujimura et al. |
| D798,316 S | 9/2017 | Bradley et al. |
| D800,912 S | 10/2017 | Uzri et al. |
| D804,497 S | 12/2017 | Akatsu et al. |
| D804,498 S | 12/2017 | Akatsu et al. |
| D805,526 S | 12/2017 | Ternoey |
| D805,527 S | 12/2017 | Ternoey |
| D805,533 S | 12/2017 | Oguchi et al. |
| D806,091 S | 12/2017 | Weaver et al. |
| D807,380 S | 1/2018 | Chen |
| 10,359,432 B2 | 7/2019 | Kipps et al. |
| 2003/0068664 A1 | 4/2003 | Albitar et al. |
| 2003/0091986 A1 | 5/2003 | Pallavicini et al. |
| 2004/0077013 A1 | 4/2004 | Ashkenazi et al. |
| 2005/0084491 A1 | 4/2005 | Shealy et al. |
| 2005/0191620 A1 | 9/2005 | McDevitt et al. |
| 2005/0208587 A1 | 9/2005 | Cardoso et al. |
| 2005/0272106 A1 | 12/2005 | Moore et al. |
| 2006/0008920 A1 | 1/2006 | Wong et al. |
| 2006/0068501 A1 | 3/2006 | Li et al. |

(Continued)

FOREIGN PATENT DOCUMENTS

| | | |
|---|---|---|
| EP | 0282308 A2 | 9/1988 |
| EP | 2982987 A1 | 2/2016 |

(Continued)

OTHER PUBLICATIONS

Ruff, L.E., Pfeilsticker, J.A., Johnsen, N.E. et al. Identification of Peptide Mimotope Ligands for Natalizumab. Sci Rep 8, 14473 (2018). (Year: 2018).*

(Continued)

*Primary Examiner* — Ellen J Marcsisin
(74) *Attorney, Agent, or Firm* — Wilson Sonsini Goodrich & Rosati

(57) ABSTRACT

Methods and assays for detecting natalizumab in a sample, natalizumab-peptide complexes in a sample, and point-of-care devices for detecting natalizumab in a sample are described herein.

12 Claims, 10 Drawing Sheets

Specification includes a Sequence Listing.

(56) References Cited

U.S. PATENT DOCUMENTS

| | | |
|---|---|---|
| 2006/0286379 A1 | 12/2006 | Gao |
| 2007/0003554 A1 | 1/2007 | Miller |
| 2007/0021591 A1 | 1/2007 | Movius et al. |
| 2007/0277105 A1 | 11/2007 | Lee et al. |
| 2009/0022623 A1 | 1/2009 | Badley et al. |
| 2010/0330585 A1 | 12/2010 | Kabri et al. |
| 2011/0117601 A1 | 5/2011 | Haberger et al. |
| 2011/0117636 A1 | 5/2011 | Bae et al. |
| 2011/0124020 A1 | 5/2011 | Kipps et al. |
| 2011/0136155 A1 | 6/2011 | Mehra et al. |
| 2011/0320130 A1 | 12/2011 | Valdes et al. |
| 2012/0220049 A1 | 8/2012 | Bunce et al. |
| 2012/0225423 A1 | 9/2012 | Schwoebel et al. |
| 2013/0040401 A1 | 2/2013 | Zin et al. |
| 2013/0065569 A1 | 3/2013 | Leipzig et al. |
| 2013/0085349 A1 | 4/2013 | Shaanan et al. |
| 2013/0130404 A1 | 5/2013 | Mehra et al. |
| 2013/0143246 A1 | 6/2013 | Nelson et al. |
| 2013/0203063 A1 | 8/2013 | Rasmussen et al. |
| 2015/0044225 A1 | 2/2015 | Ikuta et al. |
| 2015/0293086 A1 | 10/2015 | Messmer et al. |
| 2015/0301031 A1 | 10/2015 | Zin et al. |
| 2016/0274125 A1 | 9/2016 | Plavina et al. |
| 2016/0320405 A1 | 11/2016 | Barbosa |
| 2016/0362469 A1 | 12/2016 | Wang |
| 2018/0291059 A1 | 10/2018 | Messmer |
| 2019/0324044 A1 | 10/2019 | Kipps et al. |

FOREIGN PATENT DOCUMENTS

| | | |
|---|---|---|
| WO | WO-2007022557 A1 | 3/2007 |
| WO | WO-2009121024 A2 | 10/2009 |
| WO | WO-2012023053 A2 | 2/2012 |
| WO | WO-2015160834 A1 | 10/2015 |
| WO | WO-2016123105 A1 | 8/2016 |
| WO | WO-2017008844 A1 | 1/2017 |
| WO | WO-2018031887 A1 | 2/2018 |
| WO | WO-2018187333 A1 | 10/2018 |

OTHER PUBLICATIONS

Adams et al. Monoclonal antibody therapy of cancer. Nat Biotechnol. 23:1147-1157 (2005).
Barenholz et al. A peptide mimetic of the mycobacterial mannosylated lipoarabinomannan: characterization and potential applications. J Med Microbiol 56(pt 5):579-586 (2007).
Barnett et al. In-Field Implementation of a Recombinant Factor C Assay for the Detection of Lipopolysaccharide as a Biomarker of Extant Life within Glacial Environments. Biosensors (Basel) 2(1):83-100 (2012).
Bazin et al. Rapid visual tests: fast and reliable detection of ochratoxin A. Toxins (Basel) 2(9):2230-2241 (2010).
Beum et al. Three new assays for rituximab based on its immunological activity or antigenic properties: analyses of sera and plasmas of RTX-treated patients with chronic lymphocytic leukemia and other B cell lymphomas. J Immunol Methods 289(1-2)97-109 (2004).
Blasco et al. Evaluation of a peptide ELISA for the detection of rituximab in serum. J Immun Methods 325(1-2):127-139 (2007).
Bomprezzi et al. Extended interval dosing of natalizumab: a two-center, 7-year experience. Ther Adv Neurol Disord 7(5):227-231 (2014).
Breidenbach et al. Substrate recognition strategy for botulinum neurotoxin serotype A. Nature 432(7019):925-929 (2004).
Brissette et al. Identification of cancer targets and therapeutics using phage display. Curr Opin Drug Discov Devel 9:363-369 (2006).
Carping et al. 9-Fluorenylmethoxycarbonyl amino-protecting group. J Org Chem 37(22)3404-3409 (1972).
Colman et al. Effects of amino acid sequence changes on antibody-antigen interactions. Research in Immunology 145(1):33-36 (1994).
Co-pending U.S. Appl. No. 15/185,549, filed Jun. 17, 2016.
Co-pending U.S. Appl. No. 29/568.418, filed Jun. 17, 2016.
Dalakas et al. Effect of Alemtuzumab (Campath 1H) in patients with inclusion-body myositis. Brain 132:1536-1544 (2009).
Degardin et al. Understanding and fighting the medicine counterfeit market. J Pharm Biomed Anal 87:167-175 (2013).
Delano et al. Convergent solutions to binding at a protein-protein interface. Science 287(5456):1279-1283 (2000).
Ding et al. Endotoxin detection--from limulus amebocyte lysate to recombinant factor C. Subcell Biochem 53:187-208 (2010).
FDA—definition of biological product. http://www.fda.gov/Drugs/DevelopmentApprovalProcess/HowDrugsareDevelopedandApproved/ApprovalApplications/TherapeuticBiologicApplications/ucm113522.htm (Jul. 2015).
Feltrup et al. Development of a fluorescence internal quenching correction factor to correct botulinum neurotoxin type A endopeptidase kinetics using SNAPtide. Anal Chem 84(24):10549-10553 (2012).
Fernandez-Salas et al. Botulinum Neurotoxin Serotype a Specific Cell-Based Potency Assay to Replace the Mouse Bioassay. PLoS One (7(11):e49516 (2012).
Foley et al. Low body weight as a potential surrogate risk factor for progressive multifocal leukoencephalopathy (P2-244). Neurology 82(10 supp):P2.244 (2014).
Foley. Progressive escalation of natalizumab serum concentration as a potential kinetic marker for PML risk assessment. Oral communication, abstract S51.004, Apr. 2011. American Academy of Neurology. 2011.
Golden et al. Extended result reading window in lateral flow tests detecting exposure to Onchocerca volvulus: a new technology to improve epidemiological surveillance tools. PLoS One 8(7):e69231 (2013).
Hale et al. Blood concentrations of alemtuzumab and antiglobulin responses in patients with chronic lymphocytic leukemia following intravenous or subcutaneous routes of administration. Blood 104(4):948-955 (2004).
Hale. Synthetic peptide mimotope of the CAMPATH-1 (CD52) antigen, a small glycosylphosphatidylinositol-anchored glycoprotein. Immunotechnology 1(3-4):175-187 (1995).
Harlow et al. Antibodies: A Laboratory Manual. Cold Spring Harbor Laboratory Press, Cold Spring Harbor, NY, pp. 23-26 (1988).
Hyams et al. Natalizumab therapy for moderate to severe crohn disease in adolescents. J Pediatr Gastroenterol Nutr 44(2):185-191 (2007).
Jiang et al. A novel peptide isolated from a phage display peptide library with trastuzumab can mimic antigen epitope of HER-2 J Biol Chem 280(6):4656-4662 (2004).
Jilani et al. Alemtuzumab: validation of a sensitive and simple enzyme-linked immunosorbent assay. Leuk Res 28(12):1255-1262 (2004).
Joiner et al. Comparison of Endotoxin Testing Methods for Pharmaceutical Products. Int J Pharm Compd 6:408-409 (2002).
Jones et al. Development of improved SNAP25 endopeptidase immuno-assays for botulinum type A and E toxins. J Immunol Meth 329(1-2):92-101 (2008).
Khatri et al. Effect of plasma exchange in accelerating natalizumab clearance and restoring leukocyte function. Neurology 72:402-409 (2009).
Kosik et al. Studies of enzymatic cleavage of cellulose using polysaccharide analysis by carbohydrate gel electrophoresis (PACE). Methods Enzymol 510:51-67 (2012).
Laderman et al. Rapid, sensitive, and specific lateral-flow immunochromatographic point-of-care device for detection of herpes simplex virus type 2-specific immunoglobulin G antibodies in serum and whole blood. Clin Vaccine Immunol. 15(1):159-163 (2007).
Lederman et al. A single amino acid substitution in a common African allele of the CD4 molecule ablates binding of the monoclonal antibody, OKT4. Mol Immunol 28(11):1171-1181 (1991).
Lee et al. Performance improvement of the one-dot lateral flow immunoassay for aflatoxin B1 by using a smartphone-based reading system. Sensors (Basel) 13(4):5109-5116 (2013).
Lonza Limulus Amebocyte Lysate (LAL) QCL-1000. Available from: http://bio.lonza.com/uploads/txmwaxmarketingmaterial/Lonza ManualsProductInstructions CL-1000 Product Insert.pdf (2007).

(56) References Cited

OTHER PUBLICATIONS

Maloney et al. IDEC-C2B8 (Rituximab) anti-CD20 monoclonal antibody therapy in patients with relapsed low-grade non-Hodgkin's lymphoma. Blood 90(6):2188-2195 (1997).
Manshouri et al. Circulating CD20 is detectable in the plasma of patients with chronic lymphocytic leukemia and is of prognostic significance. Blood 101(7):2507-2513 (2002).
Maple et al. Development and validation of ELISA for Herceptin detection in human serum. J Immunol Methods 295:169-182 (2004).
McDade et al. What a Drop Can Do: Dried Blood Spots As A Minimally Invasive Method for Integrating Biomarkers into Population Based Research. Demography 44(4):899-925 (2007).
Merrifield et al. Solid Phase Peptide Synthesis I. J Am Chem Soc 85:2149-2154 (1963).
Messmer et al. Specific blocking to improve biopanning in biological samples such as serum and hybridoma supernatants. Biotechniques 30(4):798-802 (2001).
Messmer et al. Two human neonatal IgM antibodies encoded by different variable-region genes bind the same linear peptide: evidence for a stereotyped repertoire of epitope recognition. J Immun 162(4):2184-2192 (1999).
Miller et al. A controlled trial of natalizumab for relapsing multiple sclerosis. New Eng J Med 348(1):15-23 (2003).
Montagna et al. A new sensitive enzyme-linked immunosorbent assay (ELISA) for Alemtuzumab determination: development, validation and application. Int J Immunopathol Pharmacol 20(2):363-371 (2007).
Mulvaney et al. Incorporating fluorescent dyes and quantum dots into magnetic microbeads for immunoassays. Biotechniques. 36(4):602-609 (2004).
Nakamura et al. Lipopolysaccharide-sensitive serine-protease zymogen (factor C) found in Limulus hemocytes. Isolation and characterization. Eur J Biochem 154:511-521 (1986).
Nakano et al. ELISAs for free human immunoglobulin light chains in serum: improvement of assay specificity by using two specific antibodies in a sandwich detection method. J Immunol Methods 293:183-189 (2004).
Ouimet et al. Comparison of Fluorigenic Peptide Substrates PL50, SNAPtide, and BoTest A/E for BoNT/A Detection and Quantification: Exosite Binding Confers High-Assay Sensitivity. Journal of Biomolecular Screening 18(6):726-735 (2013).
PCT/US2009/038674 International Search Report and Written Opinion dated Dec. 24, 2009.
PCT/US2015/025796 International Search Report and Written Opinion dated Aug. 21, 2015.
PCT/US2016/014924 International Search Report and Written Opinion dated Apr. 8, 2016.
PCT/US2017/046499 International Search Report and Written Opinion dated Dec. 8, 2017.
PCT/US2017/046499 Invitation to Pay Additional Fees dated Oct. 11, 2017.
PCT/US2018/25889 International Search Report and Written Opinion dated Jul. 2, 2018.
Perosa et al. CD20 Mimicry by a mAb Rituximab-Specific Linear Peptide A Potential Tool for Active Immunotherapy of Autoimmune Disease. Ann NY Acad Sci 1051:672-683 (2005).
Perosa et al. Identification of an antigenic and immunogenic motif expressed by two 7-mer rituximab-specific cyclic peptide mimotopes: implication for peptide-based active immunotherapy. J Immunol 179(11)7967-7974 (2007).
Pierce® LAL Chromogenic Endotoxin Quantitation Kit. Available from: https://www.piercenet.com/instructions/2162445.pdf (2013).
Planas et al. Long-term safety and efficacy of natalizumab in relapsing-remitting multiple sclerosis: impact on quality of life. Patient Relat Outcome Meas 5:25-33 (2014).
Polman et al. A randomized, placebo-controlled trial of natalizumab for relapsing multiple sclerosis. New Eng J Med 354(9):899-910 (2006).
Poras et al. Detection and Quantification of Botulinum Neurotoxin Type A by a Novel Rapid In Vitro Fluorimetric Assay. Applied and Environmental Microbiology 75(13):4382-4390 (2009).
Rebello et al. Pharmacokinetics of CAMPATH-1H: assay development and validation. J Immunol Methods 260(1-2):285-302 (2002).
Rohr et al. Immunoassay employing surface-enhanced Raman spectroscopy. Anal Biochem 182(2):388-398 (1989).
Sanchez et al. A general process for the development of peptide-based immunoassays for monoclonal antibodies. Cancer Chemother Pharmacol 66(5):919-925 (2010).
Shin et al. Combinatorial solid phase peptide synthesis and bioassays. J Biochem Mol Biol 38(5):517-525 (2005).
Sosnick et al. Distances between the antigen-binding sites of three murine antibody subclasses measured using neutron and X-ray scattering. Biochemistry 31:1779-1786 (1992).
Tan et al. Pharmacokinetics of Cetuximab After Administration of Escalating Single Dosing and Weekly Fixed Dosing in Patients with Solid Tumors. Clin Cancer Res. 12(21):6517-6522 (2006).
Tian et al. Antigen peptide-based immunosensors for rapid detection of antibodies and antigens. Anal Chem 81 (13):5218-5225 (2009).
Titov et al. Development and optimization of immunoassays for the detection of botulinum toxins. Prikl Biokhim Mikrobiol 48(2):249-256 (2012).
Tokunaga et al. Further studies on lipopolysaccharide-sensitive serine protease zymogen (factorC): its isolation from Limulus polyphemus hemocytes and identification as an intracellular zymogen activated by alpha-chymotrypsin, not by trypsin. J Biochem 109:150-157. (1991).
U.S. Appl. No. 12/934,624 Office Action dated Aug. 22, 2014.
U.S. Appl. No. 12/934,624 Office Action dated Jan. 8, 2014.
U.S. Appl. No. 12/934,624 Office Action dated Mar. 27, 2015.
U.S. Appl. No. 14/686,578 Office Action dated Apr. 3, 2017.
U.S. Appl. No. 14/686,578 Office Action dated Oct. 14, 2016.
U.S. Appl. No. 14/981,715 Office Action dated Aug. 3, 2018.
U.S. Appl. No. 14/981,715 Office Action dated Jan. 19, 2017.
U.S. Appl. No. 14/981,715 Office Action dated Jul. 12, 2016.
U.S. Appl. No. 14/981,715 Office Action dated Oct. 25, 2017.
U.S. Appl. No. 15/185,549 Office Action dated Jan. 6, 2017.
U.S. Appl. No. 16/453,259 Office Action dated Aug. 13, 2019.
U.S. Appl. No. 16/453,259 Office Action dated Feb. 27, 2020.
U.S. Appl. No. 29/568,418 Office Action dated Feb. 8, 2018.
Vennegoor et al. Clinical relevance of serum natalizumab concentration and anti-natalizumab antibodies in multiple sclerosis. Mult Scler 19(5):593-600 (2013).
Wang et al. Acute intraocular inflammation caused by endotoxin after intravitreal injection of counterfeit bevacizumab in Shanghai, China. Ophthalmology 120(2):355-361 (2013).
Williams et al. Thrice-weekly low-dose rituximab decreases CD20 loss via shaving and promotes enhanced targeting in chronic lymphocytic leukemia. J Immunol 177:7435-7443 (2006).
Zhovtis et al. Extended interval dosing of natalizumab in multiple sclerosis. J Neurol Neurosurg Psychiatry 87(8):885-889 (2016).
Casey, et al. Phage display of peptides in ligand selection for use in affinity chromatography. Methods Mol Biol. 2008;421:111-24.
Murray et al. Generation and Refinement of peptide mimetic ligands for paratope-specific purification of monoclonal antibodies. Analytical Biochemistry 296:9-17 (2001).
Smith et al. Purification of anti-MUC1 antibodies by peptide mimotope affinity chromatography using peptides dervied from a polyvalent phage display library. J. Chromatogrpahy B 766:13-26 (2001).
U.S. Appl. No. 15/944,099 Office Action dated Jul. 13, 2020.
U.S. Appl. No. 16/453,259 Office Action dated Jun. 29, 2020.
Bellofiore et al. Identification and refinement of a peptide affinity ligand with unique specificity for a monoclonal anti-tenascin-C antibody by screening of a phage display library. J Chromatogr A 1107(1-2):182-191 (2006).

(56) References Cited

OTHER PUBLICATIONS

Guagnozzi et al. Natalizumab in the treatment of Crohn's disease. Biologies 2(2):275-284 (2008).
Murray et al. Purification of monoclonal antibodies by epitope and mimotope affinity chromatography. J Chromatogr A 782(1):49-54 (1997).
U.S. Appl. No. 15/944,099 Office Action dated Mar. 16, 2021.

* cited by examiner

DETECTION AND QUANTIFICATION OF NATALIZUMAB

CROSS-REFERENCE TO RELATED APPLICATIONS

This application is a U.S. National Stage Entry of PCT/US2017/046499, filed Aug. 11, 2017; which claims the benefit of U.S. Provisional Application No. 62/374,217, filed Aug. 12, 2016. Priority is claimed pursuant to 35 U.S.C. § 119. The above noted patent applications are incorporated by reference as if set forth fully herein.

STATEMENT AS TO FEDERALLY SPONSORED RESEARCH

The inventions described herein were made with the support of the United States government under grants 1R41CA192697-01 and 1R43CA183241-01 awarded by the National Institutes of Health Small Business Innovation Research (NIH-SBIR). The government has certain rights in the disclosed subject matter.

SEQUENCE LISTING

The instant application contains a Sequence Listing which has been submitted electronically in ASCII format and is hereby incorporated by reference in its entirety. Said ASCII copy, created on Aug. 10, 2017, is named 47085-712_601_SL.txt and is 10,449 bytes in size.

BACKGROUND OF THE INVENTION

Accurate drug dosing is critical for optimal patient treatment. Actual drug levels vary enormously among people given the same standard dose. Insufficient dosing can result in a poor response to treatment, whereas excessive dosing results in higher costs, wasted resources, and troublesome side effects.

Monoclonal antibodies (mAb) and other biologics are targeted therapies that are increasingly being used to treat indications such as cancer and autoimmune disease, such as multiple sclerosis (MS). MS is a leading cause of neurologic disability, and the disease is characterized by multiple inflammatory lesions and demyelination within the white matter of the central nervous system (CNS). Natalizumab (marketed as Tysabri by Biogen Idec) is the top-selling biologic drug indicated for treatment of MS and is being used to treat 25,000 to 50,000 of the 400,000 MS patients in the US.

SUMMARY OF THE INVENTION

In some embodiments, described herein are methods, assays, complexes, and devices for measuring natalizumab in a sample. In some embodiments, described herein is a method of capturing an antibody in a sample comprising contacting a sample with a peptide at least 95% identical to a peptide selected from the group consisting of SEQ ID NOs: 1-23, allowing binding of the peptide with the antibody to form an antibody-peptide complex, and detecting the antibody-peptide complex. In some embodiments, the peptide is selected from the group consisting of SEQ ID NOs:1, 2, 4, 13, 16, and 18-23. In some embodiments, the antibody is not complexed to an epitope of a target protein. In some embodiments, the antibody is natalizumab.

Also described herein are methods, assays, complexes, and device for monitoring natalizumab in a biological sample obtained from a subject. In some embodiments, the biological sample is selected from the group consisting of body fluids, tissues, body swabs, and body smears. In some embodiments, the biological sample is a fluid. In some embodiments, the fluid contains antibody at a concentration of between about 0.5 mcg/mL to 120 mcg/mL. In some embodiments, the fluid is selected from the group consisting of serum, plasma, whole blood, red blood cell concentrates, platelet concentrates, leukocytes concentrates, urine, cerebral spinal fluid, and sputum. In some embodiments, the biological sample is obtained from a human.

In some embodiments, described herein is a method of capturing natalizumab in a sample comprising contacting a sample with a peptide at least 95% identical to a peptide selected from the group consisting of SEQ ID NOs: 1-23, wherein the peptide is attached to a solid support. In some embodiments, the peptide binds to the antigen binding site of the antibody. In further embodiments, described herein is a method of capturing an antibody in a sample comprising contacting a sample with a peptide at least 95% identical to a peptide selected from the group consisting of SEQ ID NOs: 1-23, allowing binding of the peptide with the antibody to form an antibody-peptide complex, and detecting the antibody-peptide complex, wherein detection of the antibody-peptide complex is performed by detection of a detectable label on the antibody or the peptide. In further embodiments, detection of the antibody-peptide complex is performed by Western blot analysis, dot blot analysis, flow cytometry, enzyme-linked immunosorbent assay (ELISA), lateral flow immunoassay, radioimmunoassay (RIA), competition immunoassay, dual antibody sandwich assay, chemiluminescent assay, bioluminescent assay, fluorescent assay, or agglutination assay.

Also described herein is a natalizumab-mimetope complex comprising: a mimetope comprising a peptide between 7 and 26 amino acids long; and natalizumab. In some embodiments, the peptide is at least 95% identical to a peptide selected from the group consisting of SEQ ID NOs: 1-23.

Also described herein is a test device comprising: a sample pad for receiving a biologic; a conjugate pad; and a test membrane comprising at least one test line comprising a peptide at least 95% identical to a peptide selected from the group consisting of SEQ ID NOs: 1-23. In some embodiments, the conjugate pad comprises a detection reagent conjugated to a peptide at least 95% identical to the peptide in the test membrane. In some embodiments, the conjugate pad comprises a detection reagent conjugated to an antibody specific for natalizumab. In some embodiments, the conjugate pad comprises a detection reagent conjugated to a peptide at least 95% identical to the peptide in the test membrane and an antibody specific for natalizumab. In further embodiments, the antibody specific for natalizumab binds natalizumab at a variable region. In other embodiments, the antibody specific for natalizumab binds natalizumab at a constant region. In some embodiments, the test membrane further comprises at least one test line comprising an antibody specific for the natalizumab-binding mimetope peptide. In some embodiments, the antibody is natalizumab or a biosimilar thereof or a new antibody specific for the selected peptide obtained by conventional methods, such as animal immunization using the selected peptide as an immunogen.

Also described herein is a method of preventing progressive multifocal leukoencephalopathy (PML) comprising:

identifying a subject receiving antibody therapy at risk of developing PML; obtaining a biological fluid from the subject; contacting the biological fluid with a test device comprising: a sample pad for receiving the biological fluid; a conjugate pad; and a test membrane comprising at least one test line comprising a peptide at least 95% identical to a peptide selected from the group consisting of SEQ ID NOs: 1-23; and, increasing the frequency of performing the method steps based on the results obtained following the step of contacting the biological fluid with a test device. In some embodiments, the conjugate pad comprises a detection reagent conjugated to a peptide at least 95% identical to the peptide in the test membrane. In some embodiments, the conjugate pad comprises a detection reagent conjugated to an antibody specific for natalizumab. In some embodiments, the conjugate pad comprises a detection reagent conjugated to a peptide at least 95% identical to the peptide in the test membrane and an antibody specific for natalizumab. In some embodiments, the antibody specific for natalizumab binds natalizumab at a variable region. In some embodiments, the antibody specific for natalizumab binds natalizumab at a constant region. In some embodiments, the test membrane further comprises at least one test line comprising an antibody specific for the natalizumab-binding mimetope peptide. In some embodiments, the antibody is natalizumab or a biosimilar thereof or a new antibody specific for the selected peptide obtained by conventional methods, such as animal immunization using the selected peptide as an immunogen. In some embodiments, the step of increasing the frequency of performing the method steps further comprises adjusting the antibody therapy based on the results obtained following the step of contacting the biological fluid with a test device.

Also described herein is a natalizumab-binding mimetope comprising a peptide at least 95% identical to a peptide selected from the group consisting of SEQ ID NOs: 1-23. Also described herein is a method of detecting natalizumab in a biological sample comprising: contacting said biological sample with a natalizumab mimetope; allowing binding of said natalizumab mimetope with the natalizumab to form a natalizumab-natalizumab mimetope complex; and detecting the natalizumab-natalizumab mimetope complex. In some embodiments, the natalizumab mimetope is at least 95% identical to a peptide selected from the group consisting of SEQ ID NOs: 1-23. In some embodiments, the natalizumab mimetope is at least 96% identical to a peptide selected from the group consisting of consisting of SEQ ID NOs: 1-23. In some embodiments, the natalizumab mimetope is at least 97% identical to a peptide selected from the group consisting of consisting of SEQ ID NOs: 1-23. In some embodiments, the natalizumab mimetope is at least 98% identical to a peptide selected from the group consisting of consisting of SEQ ID NOs: 1-23. In some embodiments, the natalizumab mimetope is at least 99% identical to a peptide selected from the group consisting of consisting of SEQ ID NOs: 1-23. In some embodiments, the natalizumab mimetope is 100% identical to a peptide selected from the group consisting of consisting of SEQ ID NOs: 1-23.

In some embodiments, described herein are methods, assays, complexes, and devices for measuring active natalizumab in a sample. In some embodiments, described herein is a method of capturing an antibody in a sample comprising contacting a sample with a peptide at least 95% identical to a peptide selected from the group consisting of SEQ ID NOs: 24-30, allowing binding of the peptide with the antibody to form an antibody-peptide complex, and detecting the antibody-peptide complex. In some embodiments, the peptide is selected from the group consisting of SEQ ID NOs:24, 29, and 30. In some embodiments, the antibody is not complexed to an epitope of a target protein. In some embodiments, the antibody is natalizumab. In some embodiments the antibody is active natalizumab In some embodiments, described herein is a method of capturing active natalizumab in a sample comprising contacting a sample with a peptide at least 95% identical to a peptide selected from the group consisting of SEQ ID NOs: 24-30, wherein the peptide is attached to a solid support. In some embodiments, the peptide binds to the antigen binding site of the active natalizumab. In further embodiments, described herein is a method of capturing an antibody in a sample comprising contacting a sample with a peptide at least 95% identical to a peptide selected from the group consisting of SEQ ID NOs: 24-30, allowing binding of the peptide with the antibody to form an antibody-peptide complex, and detecting the antibody-peptide complex, wherein detection of the antibody-peptide complex is performed by detection of a detectable label on the antibody or the peptide. In further embodiments, detection of the antibody-peptide complex is performed by Western blot analysis, dot blot analysis, flow cytometry, enzyme-linked immunosorbent assay (ELISA), lateral flow immunoassay, radioimmunoassay (RIA), competition immunoassay, dual antibody sandwich assay, chemiluminescent assay, bioluminescent assay, fluorescent assay, or agglutination assay.

Also described herein is a natalizumab-mimetope complex comprising: a mimetope comprising a peptide at least 95% identical to a peptide selected from the group consisting of SEQ ID NOs: 24-30; and active natalizumab.

Also described herein is a test device comprising: a sample pad for receiving a biologic; a conjugate pad; and a test membrane comprising at least one test line comprising a peptide at least 95% identical to a peptide selected from the group consisting of SEQ ID NOs: 24-30. In some embodiments, the conjugate pad comprises a detection reagent conjugated to a peptide at least 95% identical to the peptide in the test membrane. In some embodiments, the conjugate pad comprises a detection reagent conjugated to an antibody specific for natalizumab. In some embodiments, the conjugate pad comprises a detection reagent conjugated to a peptide at least 95% identical to the peptide in the test membrane and an antibody specific for natalizumab. In further embodiments, the antibody specific for natalizumab binds natalizumab at a variable region. In other embodiments, the antibody specific for natalizumab binds natalizumab at a constant region. In some embodiments, the test membrane further comprises at least one test line comprising an antibody specific for the natalizumab-binding mimetope peptide. In some embodiments, the antibody is natalizumab or a biosimilar thereof or a new antibody specific for the selected peptide obtained by conventional methods, such as animal immunization using the selected peptide as an immunogen.

Also described herein is a method of preventing progressive multifocal leukoencephalopathy (PML) comprising: identifying a subject receiving antibody therapy at risk of developing PML; obtaining a biological fluid from the subject; contacting the biological fluid with a test device comprising: a sample pad for receiving the biological fluid; a conjugate pad; and a test membrane comprising at least one test line comprising a peptide at least 95% identical to a peptide selected from the group consisting of SEQ ID NOs: 24-30; and, increasing the frequency of performing the method steps based on the results obtained following the step of contacting the biological fluid with a test device. In some embodiments, the conjugate pad comprises a detection reagent conjugated to a peptide at least 95% identical to the peptide in the test membrane. In some embodiments, the conjugate pad comprises a detection reagent conjugated to an antibody specific for natalizumab. In some embodiments, the conjugate pad comprises a detection reagent conjugated to a peptide at least 95% identical to the peptide in the test membrane and an antibody specific for natalizumab. In some embodiments, the antibody specific for natalizumab binds natalizumab at a variable region. In some embodiments, the antibody specific for natalizumab binds natalizumab at a constant region. In some embodiments, the test membrane further comprises at least one test line comprising an antibody specific for the natalizumab-binding mimetope peptide. In some embodiments, the antibody is natalizumab or a biosimilar thereof or a new antibody specific for the selected peptide obtained by conventional methods, such as animal immunization using the selected peptide as an immunogen. In some embodiments, the step of increasing the frequency of performing the method steps further comprises adjusting the antibody therapy based on the results obtained following the step of contacting the biological fluid with a test device.

Also described herein is a natalizumab-binding mimetope comprising a peptide at least 95% identical to a peptide selected from the group consisting of SEQ ID NOs: 24-30. Also described herein is a method of detecting active natalizumab in a biological sample comprising: contacting said biological sample with a natalizumab mimetope; allowing binding of said natalizumab mimetope with the natalizumab to form a natalizumab-natalizumab mimetope complex; and detecting the natalizumab-natalizumab mimetope complex. In some embodiments, the natalizumab mimetope is at least 95% identical to a peptide selected from the group consisting of SEQ ID NOs: 24-30. In some embodiments, the natalizumab mimetope is at least 96% identical to a peptide selected from the group consisting of SEQ ID NOs: 24-30. In some embodiments, the natalizumab mimetope is at least 97% identical to a peptide selected from the group consisting of consisting of SEQ ID NOs: 24-30. In some embodiments, the natalizumab mimetope is at least 98% identical to a peptide selected from the group consisting of consisting of SEQ ID NOs: 24-30. In some embodiments, the natalizumab mimetope is at least 99% identical to a peptide selected from the group consisting of consisting of SEQ ID NOs: 24-30. In some embodiments, the natalizumab mimetope is 100% identical to a peptide selected from the group consisting of consisting of SEQ ID NOs: 24-30.

BRIEF DESCRIPTION OF THE DRAWINGS

FIG. 4A presents results from 2 independent experiments (mean+/−SD). The dashed line indicates OD without natalizumab present in the samples. FIG. 4B depicts results with all wells coated with 7.5 ug/mL NTZ-01-Bio (except the no coating control). Natalizumab was spiked at 2560 ng/mL and the other therapeutic monoclonal antibodies were spiked at 2000 ng/mL in human serum (0.1%).

FIG. 6A depicts a calibration curve prepared using natalizumab-spiked human serum that is exposed to 3 mM GSH for 18 hours at 37 C to generate monovalent antibody. (mean+/−SD). The absence of analyte provides an OD of 0.006+/−0.003 (not depicted; n=4; mean+/−SD). FIG. 6B depicts a precision profile determined by spiking predetermined amount of natalizumab in human-serum followed by treatment with GSH, as above. The samples were run in 6 replicates and the coefficient of variation (CV) was determined by dividing the standard deviation by the mean×100. A CV below 20% is obtained for natalizumab concentrations between 16 and 1024 ng/mL (n=4).

In FIG. 11A natalizumab-specific VERITOPE™ is the capture reagent and anti-idiotype is the competitive reagent.

DETAILED DESCRIPTION OF THE INVENTION

Figure 1:
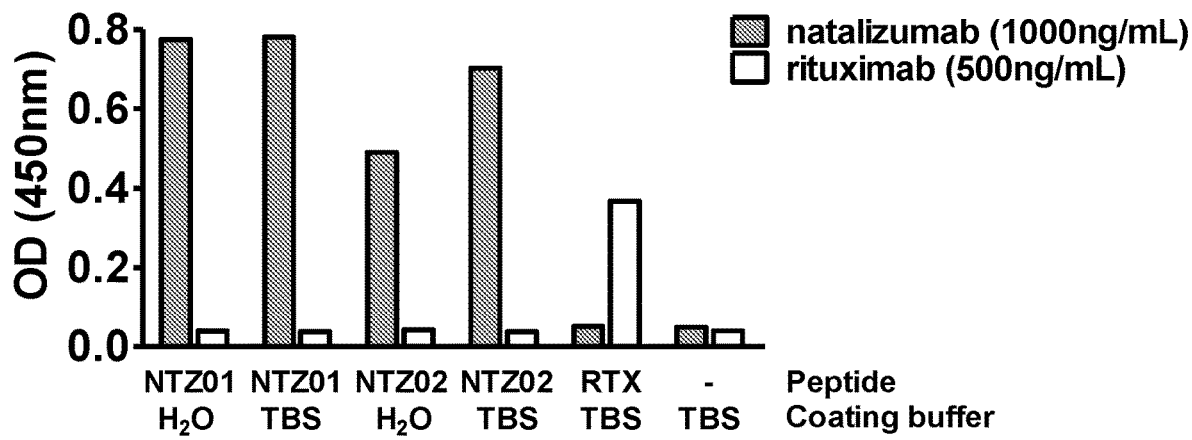
FIG. 1 is a graph showing the specificity of natalizumab (NTZ) mimetope peptides for the detection of natalizumab by enzyme-linked immunosorbent assay (ELISA).

Accurate drug dosing is critical for optimal patient treatment. There is wide variability in the actual drug levels among patients given the same standard dose. Further, the traditional model of medical sample analysis involves centralized laboratories, where tests are performed but results are delayed for hours or days. As such, medical professionals and their patients have a strong interest in obtaining precise, personalized, point-of-care diagnosis.

One example of a therapy that requires accurate drug dosing is natalizumab (marketed as Tysabri by Biogen Idec). Natalizumab is one of the most effective treatments available to reduce relapse frequency in multiple sclerosis (MS) patients. Like most mAbs, natalizumab displays highly variable pharmacokinetics (PK) across patients, compounded by the standard dosing that is not body mass or surface area adjusted. Natalizumab is the top selling biologic drug indicated for treatment of MS and is being used to treat 25,000-50,000 of the 400,000 MS patients in the US and also used in the treatment of Crohn's disease. Natalizumab is a humanized recombinant mAb that targets the α4 chain of α4β1 integrin (also known as very late activation antigen 4; VLA-4) and α4β7 integrin and is thought to function by blocking migration of immune cells across the blood-brain barrier into the central nervous system (CNS), thus suppressing inflammation in patients with relapsing-remitting multiple sclerosis (Vennegoor A, et al. *Clinical relevance of serum natalizumab concentration and anti-natalizumab antibodies in multiple sclerosis*. Mult Scler [Internet]. 2013; 19(5):593-600; Polman C H, et al., *A randomized, placebo-controlled trial of natalizumab for relapsing multiple sclerosis*. The New England Journal of Medicine. 2006 2; 354(9):899-910). Natalizumab is a full-length antibody of the IgG4 subclass and consists of two heavy and two light chains connected by four inter-chain disulfide bonds. Like other IgG4 antibodies, natalizumab demonstrates reduced binding to Fc gamma receptors and a lack of ability to fix complement in vitro. As a result, natalizumab can block interaction of α4-integrins with their cognate receptors with minimal cell killing.

Unfortunately, the cost associated with treating chronic diseases such as MS can be considerable. Natalizumab, given by infusion, is very expensive and costs approximately $4,000-5,000 for a single dose, leading to an annual cost of close to $65,000 if the drug is taken every 4 weeks as recommended on the label. Furthermore, the immunosuppressive activity of natalizumab has been associated with reawakening of JC polyomavirus, which may lead to progressive multifocal leukoencephalopathy (PML), a serious and often-fatal opportunistic brain infection. Approximately 55% of MS patients are positive for anti-JC virus antibodies, which puts them at increased risk for developing PML while on natalizumab. The estimated incidence of PML is 1:1,000 after a median of 18 months of treatment, and the mortality rate of PML patients is close to 25%, and most of the survivors of PML have permanent residual brain damage. Restoring immune function by accelerating the removal of natalizumab from the body is the only intervention for PML with demonstrated efficacy (Khatri B O, et al. *Effect of plasma exchange in accelerating natalizumab clearance and restoring leukocyte function*. Neurology. 2009; 72:402-9.). Reducing the dose of natalizumab or increasing infusion intervals could mitigate the risk of developing PML in susceptible patients (Planas R, et al. *Long-term safety and efficacy of natalizumab in relapsing-remitting multiple sclerosis: impact on quality of life*. Patient Relat Outcome Meas [Internet]. 2014; 5:25-33).

The standard dosing regimen for natalizumab is 300 mg by IV infusion every 4 weeks. The current dosing strategy for natalizumab is not customized for each patient, and there is growing evidence of considerable variability in the rate at which different patients clear the drug from their bodies. A 2011 study by Foley reported that patients with MS who were receiving monthly doses of natalizumab exhibited patient-to-patient variability in their serum natalizumab levels. Furthermore, natalizumab was found to accumulate in the serum in some patients who did not clear the drug within the 4-week period (Foley J. *Progressive escalation of natalizumab serum concentration as a potential kinetic marker for PML risk assessment*. Oral communication, abstract S51.004, April 2011. American Academy of Neurology. 2011; Bomprezzi R, et al. *Extended interval dosing of natalizumab: a two-center, 7-year experience*. Ther Adv Neurol Disord [Internet]. 2014; 7(5):227-31). Similarly, integrin saturation by natalizumab at the end of 4 weeks has been reported to range from 80% (Miller D H et al., *A controlled trial of natalizumab for relapsing multiple sclerosis*, New Eng J Med, 2003) to less than 40% (Hyams J S, et al. *Natalizumab therapy for moderate to severe crohn disease in adolescents*. J Pediatr Gastroenterol Nutr [Internet]. 2007; 44(2):185-91). Research indicates that patients with low body weight may be receiving excessive drug, which could place them at higher risk for PML (Foley J, et al., *Low body weight as a potential surrogate risk factor for progressive multifocal leukoencephalopathy*. In: Pulst S, editor. The 66th Annual Meeting of American Academy of Neurology. 2014. p. P2-244). Patients with higher levels of free, circulating natalizumab may have increased risk of PML, which could be reduced through dose extension schedules. An extended dosing schedule of 300 mg every 6 to 8 weeks has been suggested as one way to maintain the efficacy of natalizumab while reducing exposure to the drug, and thereby reducing the risk for PML (Bomprezzi R, et al. *Extended interval dosing of natalizumab: a two-center, 7-year experience*. Ther Adv Neurol Disord [Internet]. 2014; 7(5):227-31; see also, Zhovtis R., et al. *Extended interval dosing of natalizumab in multiple sclerosis*. J Neurol Neurosurg Psychiatry 2016; 87(8):885-9). Both the clinical literature and discussions with neurologists have highlighted the importance of frequent monitoring of natalizumab serum concentrations in individual patients in order to maximize drug efficacy and minimize risk for PML. However, there is currently no widely available assay enabling the measurement of natalizumab serum levels in treated patients, such as a routine, fast, easy-to-use, and inexpensive point-of-care lateral flow immunoassay for rapid measurement of natalizumab levels in a finger-stick blood sample.

Peptide-based immunoassays can be developed for monitoring mAb levels. Phage displayed peptide libraries are used to select peptide sequences that mimic the target antigen of a given mAb. Peptide libraries displayed on bacteriophage are routinely used to identify peptide epitopes, or mimetopes (also referred to as VERITOPES™), recognized by antibodies. Phage display works best with concentrated and highly purified proteins, and as such therapeutic mAb are ideal targets. When short peptides, 7 to 26 amino acids long, are screened, the selected peptides almost invariably bind to the antigen-binding site of the antibody and are competed by the natural ligand (Sanchez A B, et al. *A general process for the development of peptide-based immunoassays for monoclonal antibodies*. Cancer Chemother Pharmacol [Internet]. 2010/01/21 ed. 2010; 66(5):919-25). These mimetope peptides are then optionally used as capture or detection reagents in ELISA or other solid phase immunoassays such as lateral flow immunoassay (LFA) as long as the density of the peptide is sufficient to enable multivalent binding avidity to compensate for the moderate affinity. Mimetope peptides may also be selected from a library that contains cysteines flanking the peptide mimetope sequence to increase the stability of the peptide through disulfide bond formation. Described herein are methods, assays, complexes, and devices that incorporate mimetope peptide reagents selected for specific binding to natalizumab and assays (including LFAs and ELISAs) that implement these peptides for the capture of natalizumab from solution including biological samples for the purpose of measuring circulating natalizumab concentrations in patients for dose monitoring applications.

In some embodiments, the methods, assays, complexes, and devices described herein are useful for monitoring the level of mAb in a subject. In some embodiments, the level of mAb is monitoring using a biological sample obtained from a subject. In some embodiments, the subject is a human (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant or research mammals (such as cattle, pigs, horses, sheep, goats, dogs, cats, rabbits, rats, and/or mice); and birds (e.g., commercially relevant birds such as chickens, ducks, geese, and/or turkeys).

One advantage of the methods, assays, complexes, and devices described herein is that they provide means to detect, monitor, and record drug levels in a patient with precision directly at the point-of-care. The drugs can be novel or biosimilar drugs, and the technology is based on the binding of a mimetope to an antibody. Mimetopes are peptides that specifically detect a given biological drug (novel or biosimilar) in a biologic fluid. Mimetopes are described in U.S. Pat. No. 9,250,233, which is hereby incorporated in full by reference. The tests are optionally performed with a disposable, integrated point-of-care device, or performed with a laboratory-based enzyme-linked immunosorbent assay (ELISA), or performed with a fixed reader, as a tabletop system connected to a computer. Devices and systems for use with mimetopes include those performed with a personal point-of-care device. In some embodiments, the personal point-of-care device comprises a housing, a display, a test strip holder, a test strip comprising a peptide which binds to an antigen-binding site of an antibody present in a sample from a user, an imaging device for imaging the test strip, a processor, an onboard memory, and a communications element. In some embodiments, the personal point-of-care device includes an on-device display. In some embodiments, the display is embedded in a face of the device and the test strip holder is encased by the device. In some embodiments, the display is not attached to the device. In some embodiments, the display color, font, image size, contrast, or contents are user-selected. In some embodiments, the display may render various icons or messages to a user, such as test results, device status, or error messages. In some embodiments, the personal point-of-care device optionally includes an audio indicator or a light indicator. In further embodiments, contents of the on-display device outputs into audio by user-selection. In some embodiments, the device is reversibly connected to a mobile device, a computer, a GPS, an IPAD, a USB drive, a printer, a scanner, a television, a server, a car, a smart watch, smart glasses, an IPOD, a game player, a projector, a camera, or similar electronic devices.

The methods, assays, complexes, and devices described herein provide benefit to the patient, the medical professional, the pharmaceutical company, and the insurance company. The patient benefits by receiving the optimal dose of natalizumab (avoiding high cost and adverse side effects associated with excessive dosing such as PML, or poor response to treatment associated with insufficient dosing). The medical professional benefits with knowledge that a patient has a specific drug level. The medical professional has the information to adjust the dose accurately in order to increase or decrease the patient's response to natalizumab. The pharmaceutical company benefits by saving costs from not having natalizumab in limited supply squandered due to waste or inefficiency. Finally, the insurance company benefits by not having to purchase additional natalizumab beyond the amount needed for optimal dosing of a patient. Further, therapeutic dose monitoring of natalizumab with the methods, assays, complexes and devices described herein will enable the identification of patients who have excessive free drug levels producing potentially elevated VLA-4 receptor saturations with reduced or absent immune cell trafficking and are candidates for dose extension. The methods, assays, complexes and devices described herein are optionally also used to identify patients with sub-therapeutic drug levels and may indicate development of anti-drug antibodies. Different therapeutic interventions are performed on patients having lower drug levels (identified via the methods, assays, complexes, and devices described herein), such as increasing the dose, or frequency of dosing, to maximize therapeutic benefit, or rapidly switching to another treatment approach more likely to succeed. On the other hand, patients for which drug levels may be well above the range required for optimal clinical benefit, as identified by the methods, assays, complexes, and devices described herein, could have subsequent treatments delayed, reducing the risk of PML without affecting outcomes, or minimally be placed under closer medical monitoring based on the risk associated with elevated drug levels.

Certain Terminology

Unless otherwise defined, all technical terms used herein have the same meaning as commonly understood by one of ordinary skill in the art. As used in this specification and the appended claims, the singular forms "a," "an," and "the" include plural references unless the context clearly dictates otherwise. Any reference to "or" herein is intended to encompass "and/or" unless otherwise stated. As used herein, the term 'about' a number refers to that number plus or minus 10% of that number. The term 'about' a range refers to that range minus 10% of its lowest value and plus 10% of its greatest value.

In some embodiments, the methods, assays, complexes, and devices described herein comprise sample pads, conjugate pads, colloidal gold conjugates (or other colored or fluorescent monodispersed types of particle conjugates such as those made of latex), test lines, and/or membranes. In some embodiments, the sample pads are pretreated with blocking agents and surfactants to improve flow and subsequent release of agents from the conjugate pad. In the case of blood samples, the sample pad may also include a filter that removes cells while allowing serum or plasma to flow through to the membrane. The colloidal gold may be a monodisperse and uniform solution of 40 nm colloidal gold prepared by a reduction of aqueous $HAuCl_4$ with a cherry red appearance. For detection of test lines, mimetope peptide may be conjugated to the gold colloids by passive adsorption, and the coating density of the mimetope on the gold may be optimized to enable measurement of the proportion of bivalent natalizumab in a sample. Conjugate pad parameters, including flow rate, release characteristics, and stability, may be optimized to enable measurement of the proportion of bivalent natalizumab in a sample. Pretreatment of a conjugate pad with blocking and/or stabilizing buffers can improve these parameters. In some embodiments, colloidal gold conjugates are dried onto the pre-treated conjugate pads and are able to return to solution when sample is present.

In some embodiments, the methods, assays, complexes, and devices comprise a test line comprising a mimetope peptide specific for natalizumab that serves as the first test line to capture bivalent antibody. In some embodiments, mimetope peptides are synthesized and attached to bovine serum albumin (BSA) which greatly improves adsorption of the peptide onto the membrane. In some embodiments, natalizumab (or another antibody that specifically captures the natalizumab peptide) serves as the second test line for the competitive assay portion of the test and allows measurement of both monovalent and bivalent natalizumab. The mimetope test line concentration and the natalizumab test line concentration will be varied to optimize the quantitative feature of the test. In some embodiments, the mimetope test line concentration or natalizumab test line concentration is between 0.1 mg/mL and 2.5 mg/mL. In further embodiments, the mimetope test line concentration or natalizumab test line concentration is selected from the group consisting of 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.2 mg/mL, 1.4 mg/mL, 1.6 mg/mL, 1.8 mg/mL, 2.0 mg/mL, 2.2 mg/mL, 2.4 mg/mL, 2.6 mg/mL, 2.8 mg/mL, 3.0 mg/mL, 3.2 mg/mL, 3.4 mg/mL, 3.6 mg/mL, 3.8 mg/mL, 4.0 mg/mL, 4.2 mg/mL, 4.4 mg/mL, 4.6 mg/mL, 4.8 mg/mL, 5.0 mg/mL, 5.2 mg/mL, 5.4 mg/mL, 5.6 mg/mL, 5.8 mg/mL, and 6.0 mg/mL. In some embodiments, nitrocellulose membranes are used. Alternative membrane materials may also be used. The optimal membrane may be determined empirically by testing 5-10 different forms, varied by pore size and wicking rate. Test lines may be striped onto the membrane using an automated programmable dispenser. Membranes may be blocked to reduce non-specific binding, and blocking can influence the wicking rate.

In some embodiments, the assays described herein are shelf-stable for at least two years. Components that contribute to shelf life include the stability of the reagents, such as antibodies and peptides, as well as the physical components of the assay. Assembled assays may be stored in foil pouches with a desiccant. Long term storage tests and exposure to non-optimal conditions of the assays described herein may be performed via accelerated stability testing by varying temperature, humidity and light. In some embodiments, sample assays are incubated at 4 C, room temperature, 37 C, and 55 C, and tested at various times. One week at 55 C can simulate one year at room temperature. Humidity testing may be performed with both open and closed packages at 30% and 80% relative humidity at room temperature and 37 C. Light exposure can be performed for several weeks.

In some embodiments, the methods, assays, complexes, and devices described herein comprise specific mimetope peptide sequences for the capture and quantification of free and active natalizumab in human serum. In some embodiments, the mimetope peptide specific for natalizumab is selected from the group consisting of SEQ ID NOs: 1-23. In some embodiments, the natalizumab mimetope is at least 95% identical to a peptide selected from the group consisting of SEQ ID NOs: 1-23. In some embodiments, the natalizumab mimetope is at least 96% identical to a peptide selected from the group consisting of SEQ ID NOs: 1-23. In some embodiments, the natalizumab mimetope is at least 97% identical to a peptide selected from the group consisting of consisting of SEQ ID NOs: 1-23. In some embodiments, the natalizumab mimetope is at least 98% identical to a peptide selected from the group consisting of consisting of SEQ ID NOs: 1-23. In some embodiments, the natalizumab mimetope is at least 99% identical to a peptide selected from the group consisting of consisting of SEQ ID NOs: 1-23. In some embodiments, the natalizumab mimetope is 100% identical to a peptide selected from the group consisting of consisting of SEQ ID NOs: 1-23. In some embodiments, the mimetope peptide specific for natalizumab is selected from the group consisting of SEQ ID NOs: 24-30. In some embodiments, the natalizumab mimetope is at least 95% identical to a peptide selected from the group consisting of SEQ ID NOs: 24-30. In some embodiments, the natalizumab mimetope is at least 96% identical to a peptide selected from the group consisting of SEQ ID NOs: 24-30. In some embodiments, the natalizumab mimetope is at least 97% identical to a peptide selected from the group consisting of consisting of SEQ ID NOs: 24-30. In some embodiments, the natalizumab mimetope is at least 98% identical to a peptide selected from the group consisting of consisting of SEQ ID NOs: 24-30. In some embodiments, the natalizumab mimetope is at least 99% identical to a peptide selected from the group consisting of consisting of SEQ ID NOs: 24-30. In some embodiments, the natalizumab mimetope is 100% identical to a peptide selected from the group consisting of consisting of SEQ ID NOs: 24-30. Biotinylated peptides are optionally attached to streptavidin coated plates and used as a surrogate ligand to capture natalizumab in immunoassays. In one embodiment, an enzyme linked immunosorbent assay (ELISA) with a calibration range from 20 to 240 ng/mL (after the minimum required sample dilution) is described, corresponding to a concentration range from 5-60 ug/mL natalizumab in undiluted human serum. Such an ELISA can have an intra- and inter-assay coefficient of variations ranging from 1.0 to 7.9% and from 4.2% to 18.9%, respectively. In some embodiments, described herein is a lateral flow immunoassay with a lower bound of detection of 10 ug/mL and an upper bound of detection of 100 ug/mL.

In some embodiments, active natalizumab is distinguished from denatured or inactive natalizumab using the methods, assays, complexes, and devices disclosed. Active natalizumab, as used herein, is able to bind to alpha-4 integrin and trigger downstream events, including preventing passage of immune cells, such as white blood cells, across blood vessel walls into affected organs, such as the brain, spinal cord, and bowel. Natalizumab may be denatured or inactivated by factors such as heat, high or low pH, exposure to organic solvents, length of time, enzymes, oxidizing agents, other stress conditions, or post-translational modifications, such as but not limited to: asparagine deamidation, aspartate isomerization, methionine oxidation, and lysine glycation. Denatured or inactive natalizumab may still bind to anti-idiotype antibodies, as discussed below, but will not lead to the beneficial therapeutic effects seen in successful natalizumab treatment.

In some embodiments, the methods, assays, complexes, and devices described herein are validated using reconstructed samples and/or primary patient samples. In some embodiments, the assays described herein are evaluated using reconstructed serum samples spiked with natalizumab. To mimic the in vivo Fab-exchange behavior of natalizumab, samples can be prepared containing increasing concentrations (0 to 200 ug/mL) of natalizumab (or irrelevant mAb) spiked into serum (obtained from at least 10 different individuals) and then incubated with 0.5 mM reduced glutathione (GSH) at 37 C for 17-24 hours to form monovalent natalizumab. These suspensions can be applied to the assays (n=5 for each concentration) to determine dynamic range, sensitivity, and specificity. The intensity of each test line can be determined using an end-point reader at different time intervals (e.g., 5, 10, and 15 minutes) to identify the optimal and shortest assay time. The concentration of bivalent natalizumab and total natalizumab in each sample may also be quantified by enzyme linked immunosorbent assay (ELISA). In some embodiments, the total natalizumab concentration can be measured using the competitive assay mimetope peptide-based ELISA assay described herein. In some embodiments, quantitation of the bivalent form of natalizumab is determined using a double antigen sandwich ELISA with peptide coated on the bottom of the plate as the capture reagent and peptide conjugated to horseradish peroxidase (HRP) as the detection reagent. In some embodiments, two separate test strips are run in parallel in the same cassette to independently measure bivalent and total natalizumab. In other embodiments, a single test strip accurately measures both bivalent and total natalizumab in a sample. In other embodiments, the natalizumab test line is replaced with anti-human IgG4 Fc to capture both forms of natalizumab via a sandwich format (which may also capture endogenous IgG4 if present).

In some embodiments, the assays described herein may be cross-validated against a minimum number of primary patient samples (e.g., 20 samples). In some embodiments, the samples are isolated from MS patients receiving natalizumab therapy and have known natalizumab concentrations determined by a separate, non-mimetope peptide-based and validated ELISA. In some embodiments, the assay time is less than 15 minutes. In some embodiments, the assay uses 10-40 uL of serum and 40-200 uL of chase buffer. In some embodiments, the assay uses 10-40 uL of whole blood and 40-200 uL of chase buffer. In some embodiments, the assay uses 15 uL of serum and 85 uL of chase buffer. In other embodiments, the assay uses 15 uL of whole blood and 85 uL of chase buffer.

In some embodiments, the methods, assays, complexes, and devices described herein comprise a personal point-of-care device. In some embodiments, the personal point-of-care device comprises a housing, a display, a test strip holder, a test strip comprising a peptide which binds to the antigen-binding site of natalizumab present in a sample from a user, an imaging device for imaging the test strip, a processor, an onboard memory, and a communications element. In some embodiments, the peptide comprises a sequence selected from the group consisting of SEQ ID NOs:1-28. In some embodiments, the peptide comprises a sequence selected from the group consisting of SEQ ID NOs:1-30. In further embodiments, the peptide comprises a sequence selected from the group consisting of SEQ ID NO:1, 2, 4, 13, 16, 18, 19, 20, 21, 22, 23, 24, 25, 26, 27, and 28. In further embodiments, the peptide comprises a sequence selected from the group consisting of SEQ ID NO:1, 2, 4, 13, 16, 18, 19, 20, 21, 22, 23, 24, 25, 26, 27, 28, 29, and 30. In further embodiments, the peptide comprises a sequence selected from the group consisting of SEQ ID NOs:24, 27, and 28. In further embodiments, the peptide comprises a sequence selected from the group consisting of SEQ ID NOs:24, 27, 28, 29, and 30. In some embodiments, the peptide is at least 95%, at least 96%, at least 97%, at least 98%, or at least 99% identical to a sequence selected from the group consisting of SEQ ID NO:1-30. In some embodiments, the peptide is at least 95%, at least 96%, at least 97%, at least 98%, or at least 99% identical to a sequence selected from the group consisting of SEQ ID NO:24, 29 and 30. In some embodiments, the peptide is at least 95%, at least 96%, at least 97%, at least 98%, or at least 99% identical to SEQ ID NO:29. In some embodiments, the peptide is at least 95%, at least 96%, at least 97%, at least 98%, or at least 99% identical to SEQ ID NO: 30.

In some embodiments, the personal point-of-care device includes an on-device display. In some embodiments, the display is embedded in the face of the device and the test strip holder is encased by the device. In some embodiments, the display is not attached to the device. In some embodiments, the display color, font, image size, contrast, or contents are user-selected. In some embodiments, the display may render various icons or messages to a user, such as test results, device status, or error messages. In some embodiments, the personal point-of-care device optionally includes an audio indicator. In further embodiments, contents of the on-display device outputs into audio by user-selection. In some embodiments, the device is reversibly connected to a mobile device, a computer, a GPS, an IPAD, a USB drive, a printer, a scanner, a television, a server, a car, a smart watch, smart glasses, an IPOD, a game player, a projector, a camera, or similar electronic devices. In some embodiments, the device is connected via Bluetooth. In some embodiments, the device is reversibly connected to a wearable device, such as a Fitbit®.

While preferred embodiments have been shown and described herein, it will be obvious to those skilled in the art that such embodiments are provided by way of example only. It should be understood that various alternatives to the embodiments described herein may be employed in practicing the inventions described herein.

EXAMPLES

The following illustrative examples are representative of embodiments of the methods, assays, complexes, and devices described herein and are not meant to be limiting in any way.

Example 1: Detection and Quantification of Natalizumab in Human Serum by Veritope™ Peptide-Based ELISA In one embodiment, detection and quantification of natalizumab in human serum is measured using the following peptide-based ELISA protocol. The day before the experiment, generate monovalent natalizumab by preparing suspensions of human serum containing 3 mM reduced glutathione (GSH) and different concentrations of natalizumab (256, 128, 64, 32, 16, 8 or 4 ug/mL (and 0)) to create a calibration curve. Incubate samples overnight at 37 C.

The day of the experiment: prepare a suspension of the peptide of interest (7.5 ug/mL in 1×TBS) and add to a neutravidin coated plate (or TBS only as background control). Incubate peptide on the plate for 1 h at room temperature (RT), then wash 5 times with TBST (1×TBS+0.05% Tween20).

Block nonspecific binding to the plate with the addition of 5% goat serum, then incubate 1 h at RT.

Use the monovalent natalizumab suspensions prepared in GSH-serum in the first step above as calibrators. Prepare ½₅₀ dilutions in dilution buffer (2.5% BSA-TBST) to obtain a calibration curve ranging from 1024 to 16 ng/mL natalizumab.

Wash wells 5 times with TBST and add samples in triplicate to the appropriate peptide-coated wells and to uncoated wells as background control for each sample. Incubate samples for 1 h at RT, and then wash 5 times with TBST. Add HRP-conjugated mouse monoclonal anti-human IgG4 Fc diluted 1:2000 in 1×TBST to the wells, then incubate for 30 min at RT.

Wash wells 10 times with TBST, then add TMB substrate. After a 5 minute incubation at RT, stop the reaction with 1M $H_2SO_4$ and immediately measure optical density at 450 nm using a plate reader.

Example 2: Identification of Mimetope Sequences

Mimetope peptides were selected from phage display libraries, some of which contain cysteines flanking the peptide mimetope sequence to increase stability of the peptide through disulfide bond formation. After three rounds of selection with multiple phage display libraries, individual phage plaques were isolated and sequenced. Twenty-three unique phage displayed peptide sequences were identified and are presented in Table 1.

TABLE 1

List of Natalizumab Peptide Sequences Identified by Phage Display

NEB PhD C7C Library

ACPMNESKFCGGG (SEQ ID NO: 1)

ACPSNPSKFCGGG (SEQ ID NO: 2)

ACNWMINKECGGG (SEQ ID NO: 3)

ACPKNPNKFCGGG (SEQ ID NO: 4)

ACVPSKPGLCGGG (SEQ ID NO: 5)

TABLE 1-continued

List of Natalizumab Peptide Sequences Identified by Phage Display

NEB PhD 12 Library

NFLGAVAKGAIHGGG (SEQ ID NO: 6)

HASWLGSSSNVRGGG (SEQ ID NO: 7)

TAMASTSTMLQHGGG (SEQ ID NO: 8)

HFINVSGLATVFGGG (SEQ ID NO: 9)

RDYHPRDHTATWGGG (SEQ ID NO: 10)

QMAMEQTNADYQGGG (SEQ ID NO: 11)

LPTNESSPKGSNGGG (SEQ ID NO: 12)

QTLNHSWLHTFIGGG (SEQ ID NO: 13)

VSRPAETTPRLTGGG (SEQ ID NO: 14)

Custom 7C7C7 Library

SPFHSPRCGTANSYSCLHMKITSGGG (SEQ ID NO: 15)

IYAAYPPCPQNLSKFCRHSSSPGGGG (SEQ ID NO: 16)

VENPWNQCMKGTFKRCSYPRIANGGG (SEQ ID NO: 17)

AYPHGRSCPQNISKFCFDHEKTNGGG (SEQ ID NO: 18)

QGGEWHRCMSEEGKHCVDIQFIRGGG (SEQ ID NO: 19)

TSLTVMTCPHNPSKWCSPLPAAVGGG (SEQ ID NO: 20)

AMASSATCTKPNSYSCLHAKLVPGGG (SEQ ID NO: 21)

MPSPPKNCSKFHSALCKGVTWNVGGG (SEQ ID NO: 22)

SHPQEFWCPQNFSKFCSRSYSNTGGG (SEQ ID NO: 23)

All of these unique phage clones were individually amplified and purified, and their ability to specifically bind natalizumab-coated wells was assessed. Of the twenty-three phage clones, eleven demonstrated specific binding to natalizumab (SEQ ID NOs: 1, 2, 4, 13, 16, and 18-23; peptide sequences shown in bold in Table 1). Selected peptides derived from validated phage clones were chemically synthesized with an N-terminal acetyl modification (in some cases), C-terminal biotin modification via a terminal lysine (all peptides), and a disulfide bridge between cysteines 2 and 10 or cysteines 8 and 16 by a contract peptide manufacturer, as shown in Table 2. SEQ ID NOs:29 and 30 were identified by affinity maturation of SEQ ID NO:1 and synthesized with the C-terminal Lys(Biotin).

TABLE 2

Synthetic Mimetope Peptides

| Peptide motif | Peptide name | Peptide sequence |
|---|---|---|
| 1 | NTZ-01-Bio | Ac-ACPMNESKFCGGG{Lys(Biotin)} with Cys2-Cys10 bridge (SEQ ID NO: 24) |
| 2 | NTZ-02-Bio | Ac-ACPSNPSKFCGGG{Lys(Biotin)} with Cys2-Cys10 bridge (SEQ ID NO: 25) |
| 4 | NTZ-03-Bio | Ac-ACPKNPNKFCGGG{Lys(Biotin)} with Cys2-Cys10 bridge (SEQ ID NO: 26) |
| 18 | NTZ-04-Bio | AYPHGRSCPQNISKFCFDHEKTNGGG{Lys(Biotin)} with Cys8-Cys16 bridge (SEQ ID NO: 27) |

TABLE 2-continued

Synthetic Mimetope Peptides

| Peptide motif | Peptide name | Peptide sequence |
|---|---|---|
| 23 | NTZ-05-Bio | SHPQEFWCPQNFSKFCSRSYSNTGGG{Lys(Biotin)} with Cys8-Cys16 bridge (SEQ ID NO: 28) |
| | NTZ-06-Bio | ACPRNESKFCGGG{Lys(Biotin)} with Cys2-Cys10 bridge (SEQ ID NO: 29) |
| | NTZ-07-Bio | ACPKNPSKFCGGG{Lys(Biotin)} with Cys2-Cys10 bridge (SEQ ID NO: 30) |

Synthetic peptides were supplied as TFA salt at >84% purity confirmed by mass spec and HPLC. Peptides were reconstituted and concentration was determined using a NanoDrop spectrophotometer.

Example 3: Validation of Mimetope Specificity and Assay Performance

Figure 2:
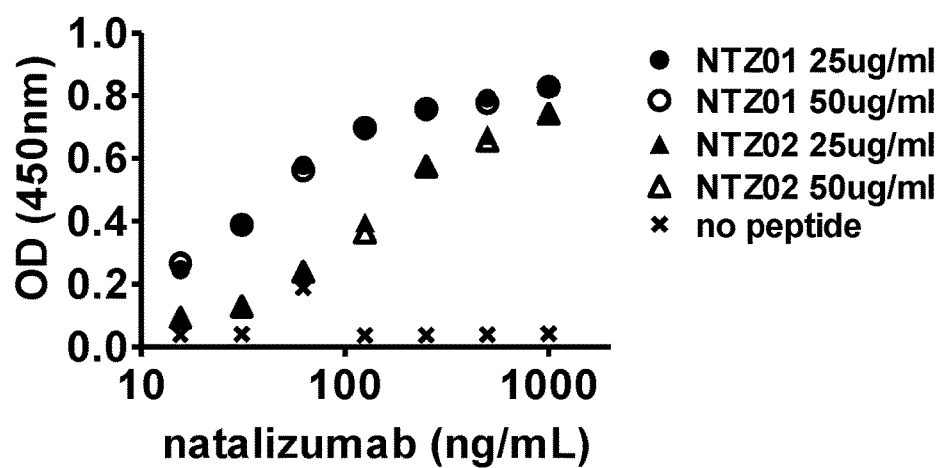
FIG. 2 is a graph showing the sensitivity of a natalizumab (NTZ) mimetope peptide-based enzyme-linked immunosorbent assay (ELISA) for natalizumab spiked in 2.5% BSA/TBST buffer. NTZ-01-Bio and NTZ-02-Bio peptides were coated at 25 ug/mL or 50 ug/mL in TBS.
Figure 3:
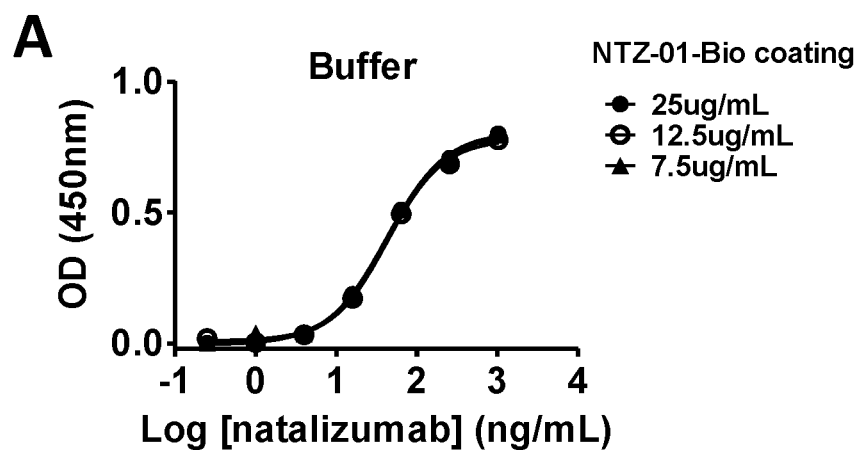
FIGS. 3A-3C are graphs showing a titration of the NTZ-01-Bio peptide coating concentration and calibration curves of natalizumab prepared in buffer (TBST-2.5% BSA) and human serum (0.1%).
Figure 3:
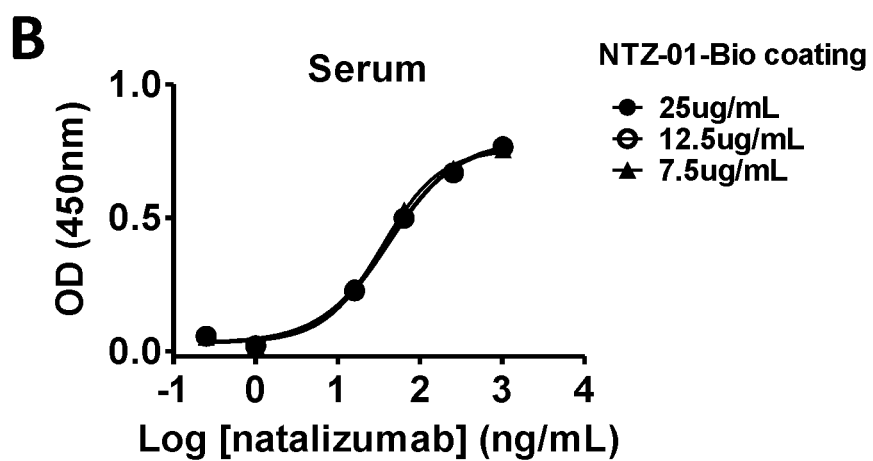
Figure 3:
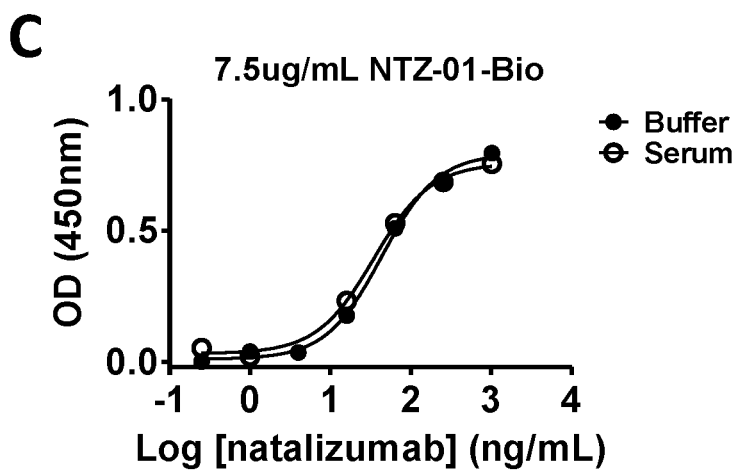
Figure 4:
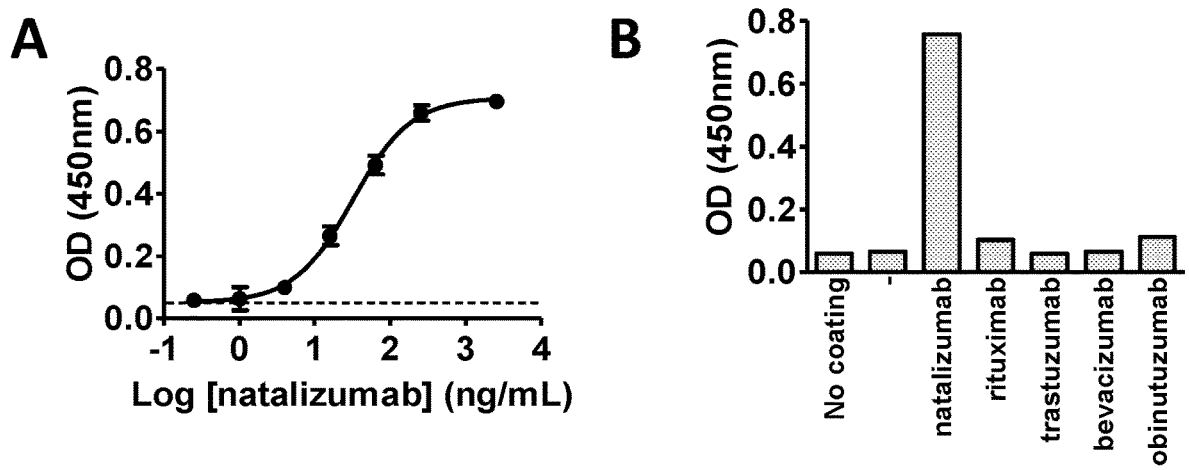
FIGS. 4A and 4B are graphs showing the sensitivity and specificity of the NTZ-01-Bio mimetope peptide-based ELISA for natalizumab spiked in human serum (0.1%).
Figure 5:
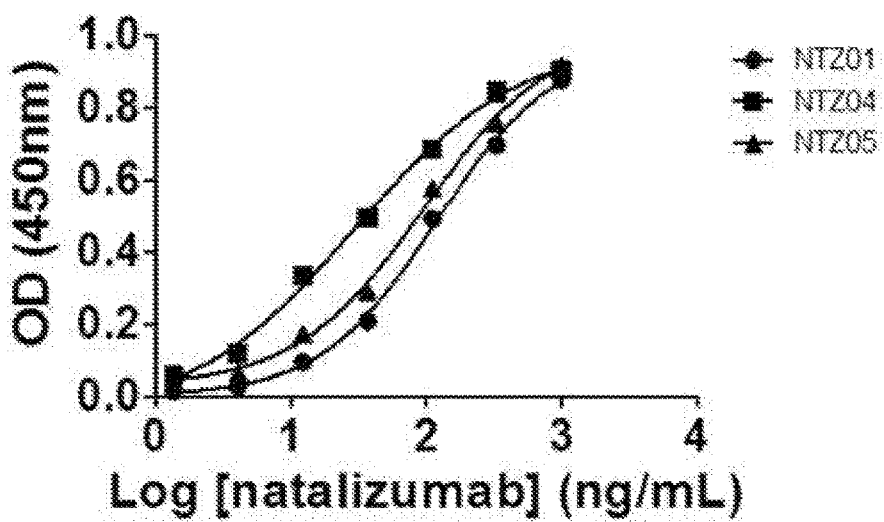
FIG. 5 is a graph illustrating the sensitivity of the NTZ-01-Bio, NTZ-04-Bio, and NTZ-05-Bio mimetope peptide-based ELISAs for natalizumab spiked in human serum (0.4%). Results from a single experiment are presented. All wells were coated with 9 uM peptide except no coating control. The calibration curve was prepared using natalizumab-spiked human serum and exposed to 3 mM GSH for 18 hours at 37 C to generate monovalent antibody.
Figure 6:
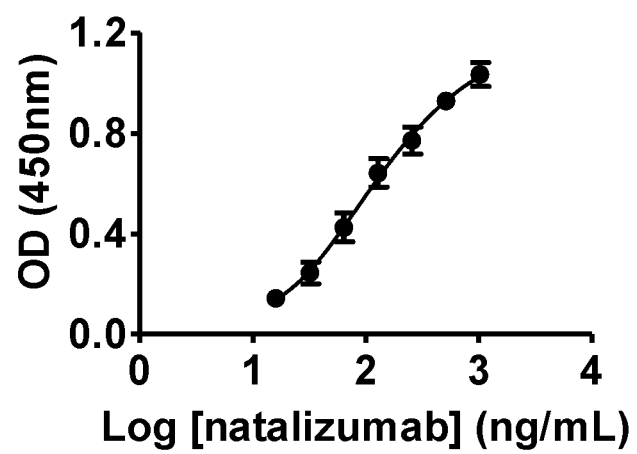
FIGS. 6A and 6B are graphs illustrating the detection of the monovalent form of natalizumab in human serum (0.4%) using the mimetope peptide-based ELISA (NTZ-01-Bio).
Figure 6:
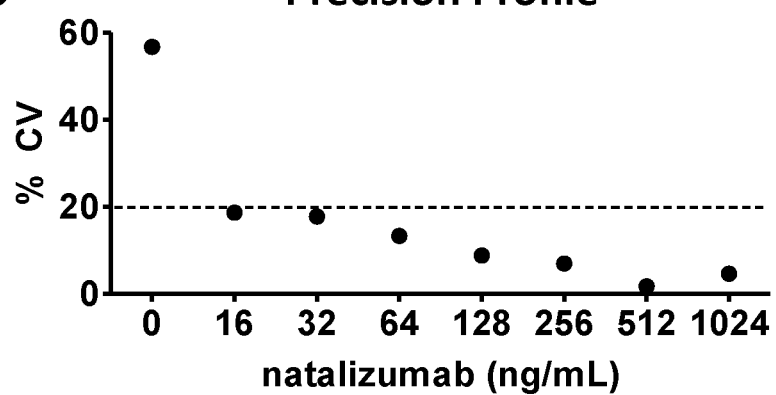

Synthesized peptides were validated for specificity by using them as ELISA capture reagents on neutravidin-coated plates. The results are shown in FIG. 1. Briefly, biotinylated peptides were coated on the wells at 100 ug/mL concentration in either tris buffered saline buffer (TBS) or water. Wells were blocked and then either natalizumab (NTZ) or rituximab (RIT) antibodies spiked in 2.5% BSA/TBST buffer at 1000 ng/mL or 500 ng/mL were added to the wells. Antibody that was captured by the peptides was subsequently detected using a goat anti-human IgG-Fc conjugated to horseradish peroxidase (HRP) combined with a colorimetric substrate. Sensitivity of the mimetope peptide for detection of natalizumab in buffer was determined, and the results presented in FIG. 2. The minimal coating concentration of peptide (NTZ-01) to achieve desired sensitivity in buffer and human serum (0.1%) was determined, as shown in FIG. 3. Sensitivity of different mimetope peptides (NTZ-01, NTZ-04, and NTZ-05) for detection of natalizumab (monovalent form) in human serum was determined, and the results are presented in FIGS. 4 and 5. Assay performance was further assessed for the detection of the monovalent form of natalizumab in human serum (0.4%) using NTZ-01 mimetope peptide-based ELISA, as depicted in FIG. 6. Spike and recovery experiments were performed where predetermined amounts (nominal concentrations) of natalizumab were spiked into human serum followed by treatment with GSH. The percent of recovery was calculated as follow: calibrated concentration/nominal concentration×100. The results are presented in Table 3:

TABLE 3

Spike and Recovery

| Nominal concentration (ng/mL) | % recovery | |
|---|---|---|
| | Mean | SD |
| 480 | 88 | 11 |
| 240 | 104 | 3 |
| 80 | 115 | 6 |
| 20 | 112 | 11 |

The dynamic range of the assay is between 20 and 240 ng/mL of natalizumab. This allows for the accurate quantification of samples containing between 5 and 60 ug/mL natalizumab after applying the minimum sample dilution required for the assay.

Example 4: Measurement of Natalizumab Levels in Human Serum

Figure 7:
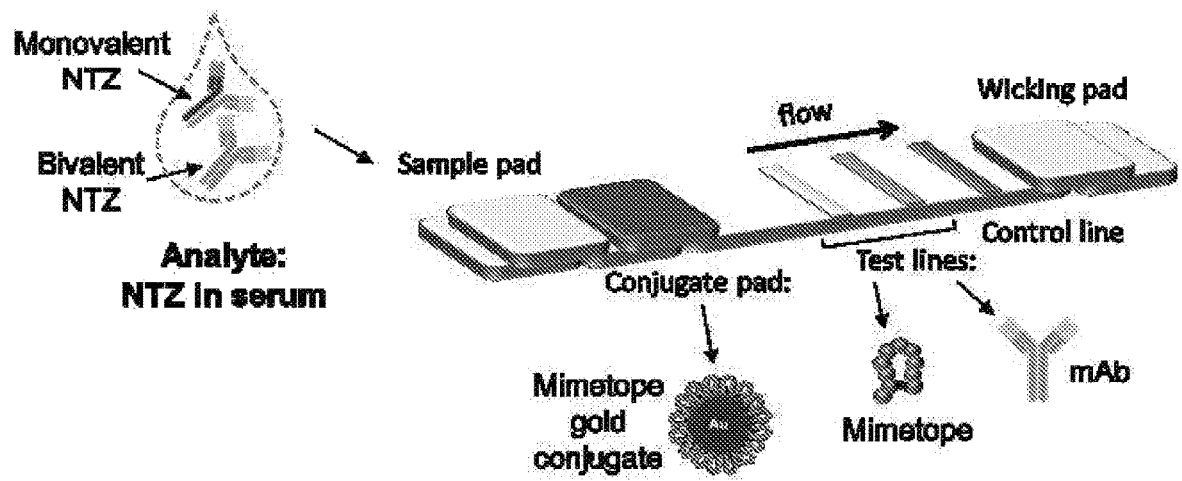
FIG. 7 depicts an exemplary lateral flow immunoassay (LFA) device for rapid measurement of natalizumab levels in a finger-stick blood sample.

A subject undergoing natalizumab therapy has her finger pricked using a lancet. A fixed and predetermined volume of blood (specific for each test) is collected using a transfer pipet and applied to a test device as shown in FIG. 7. IgG4 antibodies such as natalizumab (NTZ) can exchange Fab-arms with other endogenous IgG4 molecules, leading to the formation of monovalent molecules (hybrid IgG4 molecules with only one arm targeting VLA-4) in addition to the original bivalent form. This test measures both bivalent and total circulating levels of NTZ in the biologic sample. The conjugate pad contains colloidal gold conjugated to mimetope peptide specific for NTZ. The first test line, coated with mimetope peptide, captures bivalent NTZ via one Fab arm while the other Fab arm is detected by the mimetope-gold conjugate (i.e., a double antigen sandwich assay). The second test line is coated with NTZ antibody. When no or little NTZ is present in the sample, the mimetope-gold conjugate binds to the NTZ test line and the line develops color. If sufficient NTZ is present in the sample, both bivalent and monovalent forms compete with the NTZ test line for binding to the mimetope-gold conjugate and less color develops on the test line in a dose-dependent manner (i.e., a competitive assay). The independent control line indicates that the device ran properly. The intensity of the color changes are measured and quantified by an end-point reader.

Figure 8:
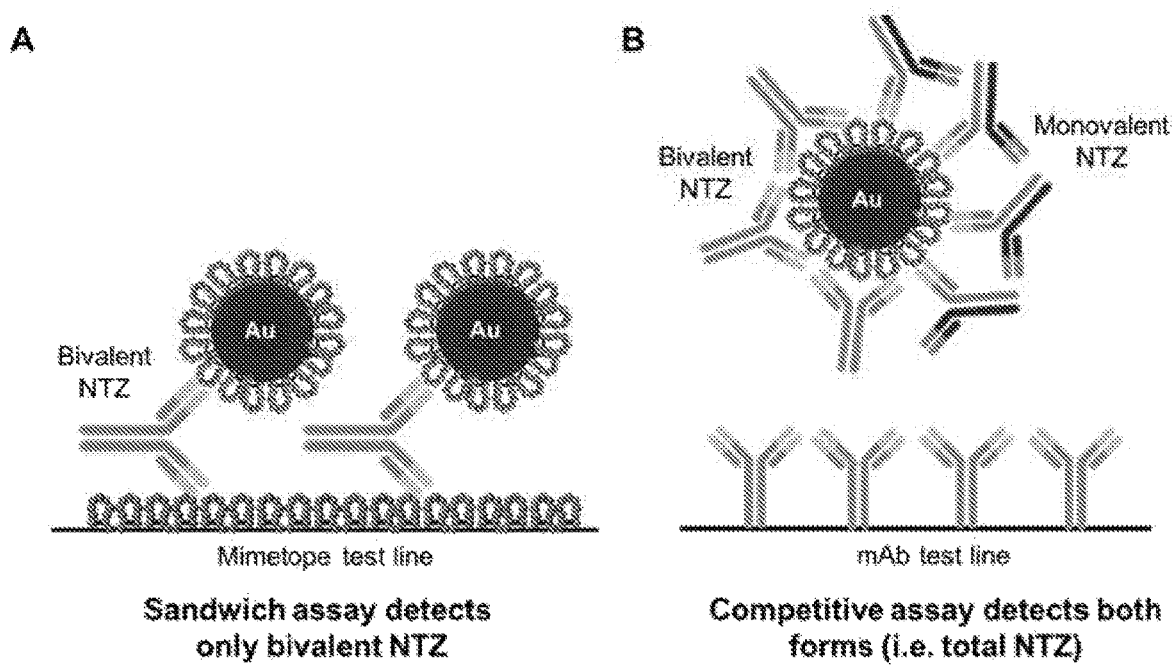
FIG. 8 depicts detection of free natalizumab levels using a combination of sandwich and competitive assays in the same lateral flow immunoassay (LFA).

This lateral flow immunoassay (LFA) design is able to measure both bivalent and total circulating levels of natalizumab in biologic samples, as shown in FIG. 8. When sufficient bivalent natalizumab (NTZ) is present in the sample, one arm of the mAb will bind to the mimetope test line and the other arm will bind to the mimetope-gold conjugate (i.e., a double antigen sandwich), as shown in FIG. 8A. This enables exclusive detection of the bivalent form because only natalizumab with both Fab-arms can bind to mimetope-gold conjugate and simultaneously bind mimetope on the test line. In the competitive test, shown in FIG. 8B, both bivalent and monovalent forms compete with the test line for binding to the mimetope-gold conjugate and less color is observed on the test line. The coating densities of the mimetope on the gold, the mimetope on the first test line, and the antibody on the second test line are optimized to enable measurement of bivalent and total natalizumab in the sample to fall within the dynamic range. Test line intensity is quantified by an off-the-shelf end-point digital reader.

Example 5: Natalizumab-Specific VERITOPE™ Inhibition of Natalizumab Binding

Figure 9:
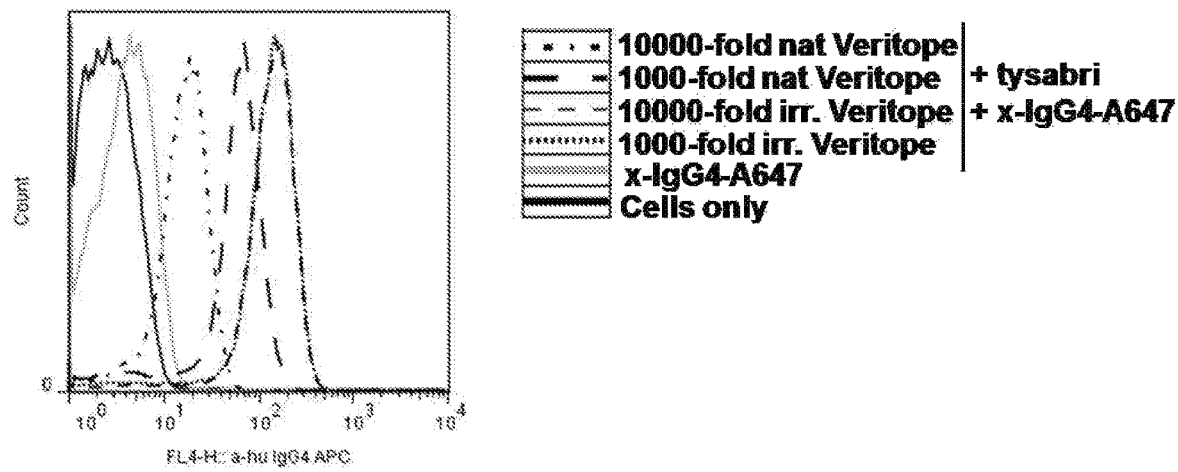
FIG. 9 depicts a flow cytometry histogram of binding between natalizumab and its cellular target, following incubation of natalizumab with varying concentrations of either a natalizumab-specific VERITOPE™ or an irrelevant peptide. Jeko-1 cells, expressing CD49d, were used as a model.

Natalizumab was incubated with increasing concentrations of natalizumab-specific VERITOPE™ (NTZ-01-Bio; SEQ ID NO:24) or irrelevant peptide (1,000 or 10,000 fold molar excess) and binding to its cellular target was measured by flow cytometry. Jeko-1 cells, expressing CD49d, were used as a model. As shows in FIG. 9, natalizumab-specific VERITOPE™ can inhibit binding of natalizumab to its cell surface target. The histogram peaks, from left to right, are: Jeko-1 cells only; x-IgG4-A647; 10,000-fold natalizumab-specific VERITOPE™; 1,000-fold natalizumab-specific VERITOPE™; 1,000-fold irrelevant VERITOPE™; and 10,000-fold irrelevant VERITOPE™.

Figure 10:
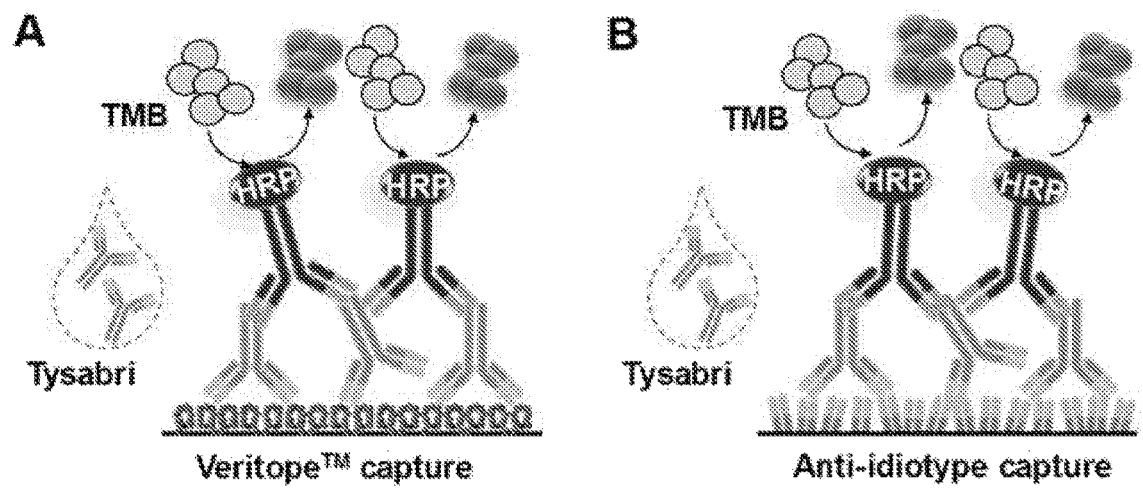
FIGS. 10A and B depicts a graphical comparison of a natalizumab-specific VERITOPE™ (FIG. 10A) and anti-idiotype (FIG. 10B) ELISA binding.
Figure 11:
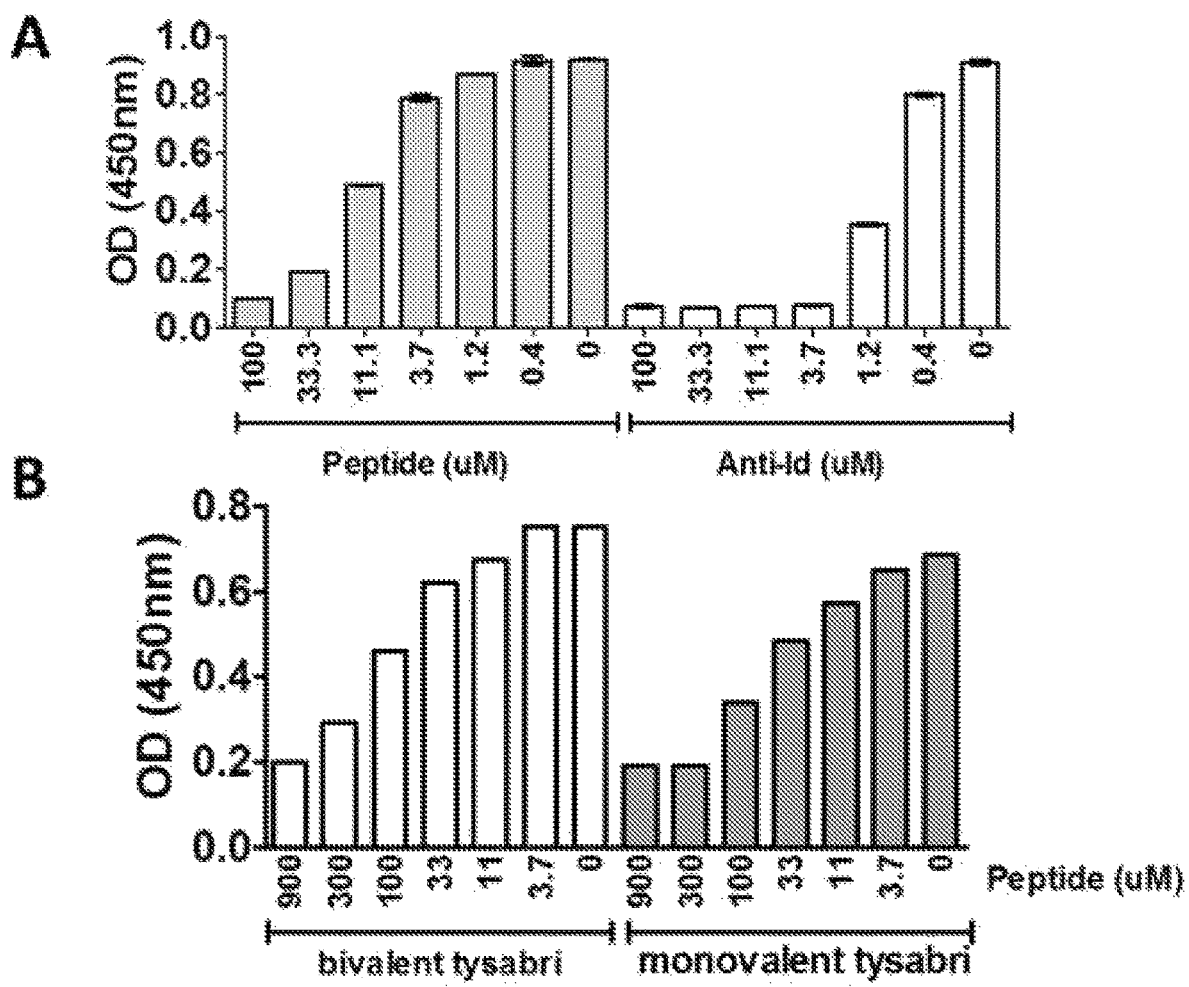
FIGS. 11A and B illustrate the characterization of a natalizumab-specific VERITOPE™ (NTZ-01-Bio; SEQ ID NO:24) and an anti-idiotype.
In FIG. 11B, anti-idiotype is the capture reagent and natalizumab-specific VERITOPE™ is the competitive reagent.
Figure 12:
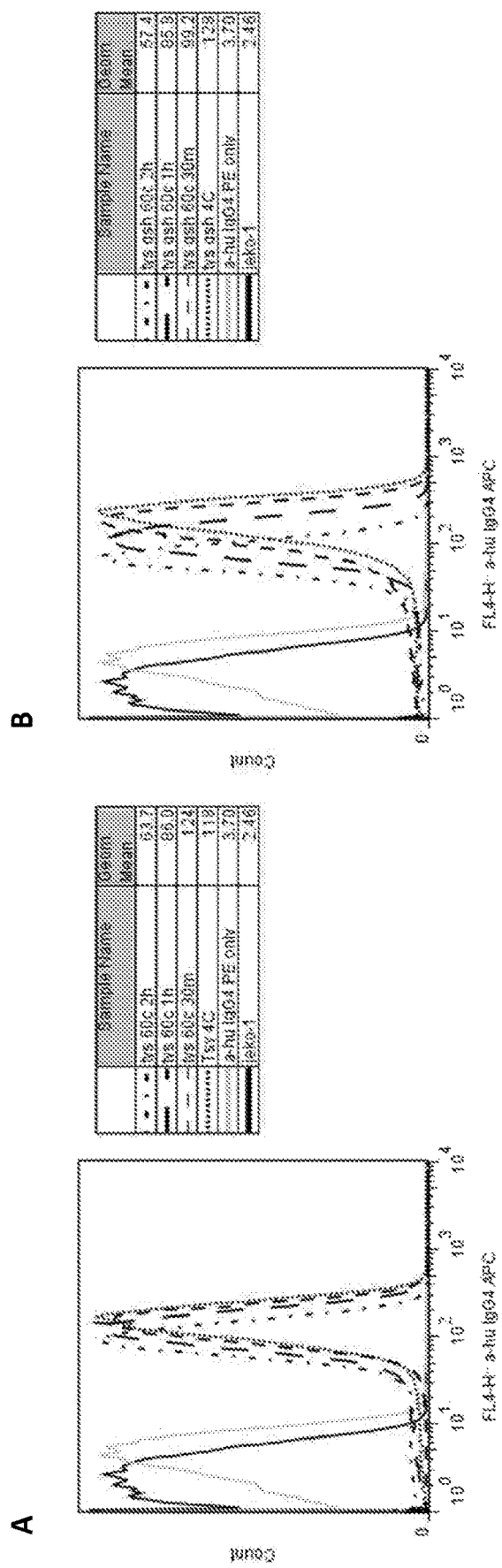
FIGS. 12A and B demonstrate that heat-inactivation of natalizumab alters bivalent natalizumab (FIG. 12A) and arm-exchanged (bispecific) natalizumab (FIG. 12B) binding to its cellular target.

Example 6: Comparison of VERITOPE™ and Anti-Idiotype ELISA for Natalizumab Monitoring A commercially available Type 1 anti-idiotype antibody Fab fragment was obtained (AbD21375; BIO-RAD) and compared to a natalizumab-specific VERITOPE™ (NTZ-01-Bio; SEQ ID NO:24). FIGS. 10A and B illustrates a comparison of VERITOPE™ (FIG. 10A) and anti-idiotype (FIG. 10B) ELISA binding. The anti-idiotype antibody (Type 1 or neutralizing) binds to the antigen binding site of natalizumab, specifically recognizes free natalizumab but not free human alpha-4/beta-1 integrin, and is suitable for pharmacokinetic (PK) studies. FIGS. 11A and B demonstrate that both VERITOPE™ (FIG. 11A) and anti-idiotype (FIG. 11B) bind to the same region of natalizumab, most likely the antigen binding site. In FIG. 11A, the natalizumab-specific VERITOPE™ is attached to the surface of the plate as the capture reagent for natalizumab (TYSABRI™), and natalizumab-specific VERITOPE™ (left side) or the anti-idiotype (right side) at different concentrations is the competitive reagent. In FIG. 11B, the anti-idiotype is attached to the surface of the plate as the capture reagent for bivalent (left side) or bispecific (monovalent; right side) natalizumab (TYSABRI™) and the natalizumab-specific VERITOPE™ is the competitive reagent. FIGS. 12A and B demonstrate that heat-inactivation of natalizumab alters natalizumab binding to its cellular target. Natalizumab was heat-inactivated by incubation at 60° C. for various periods of time. Alteration of the binding capacity of natalizumab to its cellular target was measured by flow cytometry. Jeko-1 cells, expressing CD49d, were used as a model. FIG. 12A is the bivalent natalizumab and FIG. 12B is the arm-exchanged (bispecific) natalizumab.

Figure 13:
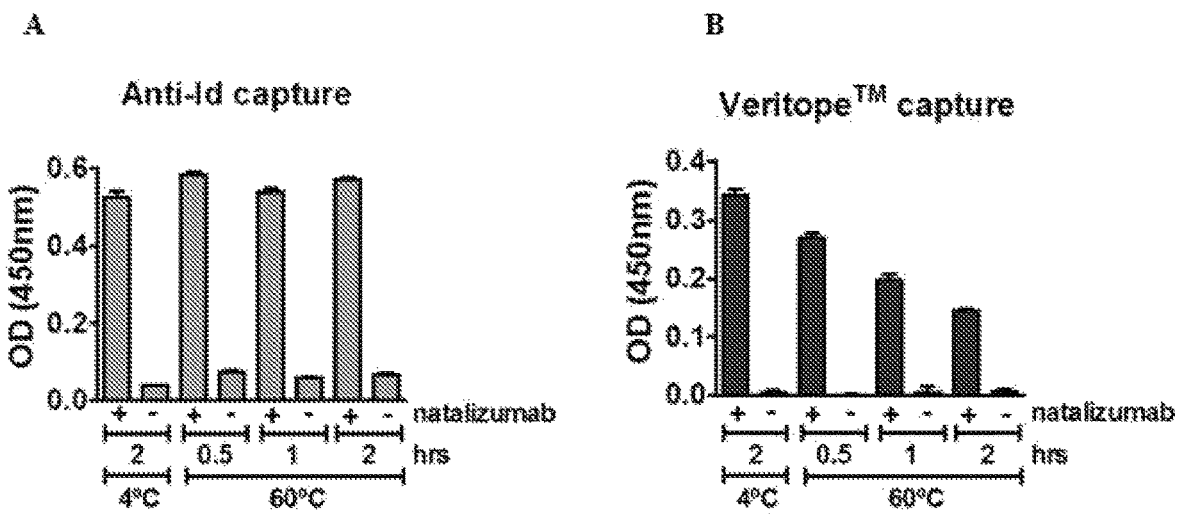
FIGS. 13A and B depict a comparison between anti-idiotype ELISA (FIG. 13A) and natalizumab-specific VERITOPE™ (FIG. 13B; NTZ-01-Bio; SEQ ID NO:24).

Example 7: VERITOPE™ ELISA Specifically Captures Active Drug Compared to Anti-Idiotype ELISA FIGS. 13A and B depict a comparison between anti-idiotype ELISA (FIG. 13A) and VERITOPE™ ELISA (FIG. 13B), demonstrating that VERITOPE™ ELISA is more sensitive than anti-idiotype ELISA to changes that affect the binding pocket of natalizumab. Natalizumab was heat-inactivated by incubation at 60° C. for various periods of time. The ability of anti-idiotype and VERITOPE™ (NTZ-01-Bio; SEQ ID NO:24) capture reagents to distinguish between active and inactive drug was measured by ELISA. Anti-idiotype ELISA measures both inactive and active drug whereas VERITOPE™ ELISA selectively distinguishes & quantifies active drug.

Example 8: Natalizumab VERITOPE™ ELISA Assay Specifications

Figure 14:
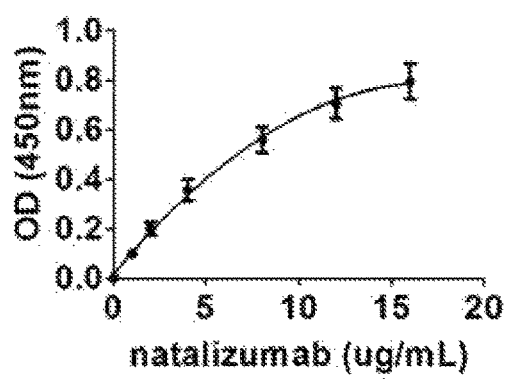
FIG. 14 depicts natalizumab-specific VERITOPE™ (NTZ-01-Bio; SEQ ID NO:24) ELISA assay calibration curve.

The natalizumab-specific VERITOPE™ (NTZ-01-Bio; SEQ ID NO:24) was characterized by a CLIA-certified/CAP-accredited lab and the assay specifications are presented in FIG. 14. The Lower Limit of Quantification (LLOQ) is 2.0 ug/mL natalizumab in undiluted serum, which corresponds to 8 ng/mL after applying the minimum required dilution of 1/250; the Upper Limit of Quantification (ULOQ) is 16.0 ug/mL natalizumab in undiluted serum, which corresponds to 64 ng/mL after applying the minimum required dilution of 1/250; the data presented are from 5 independent runs, each sample ran in triplicates (mean+/−SD) (Limit of Blank: 0.6 ug/mL; Limit of Detection: 0.8 ug/mL). Intra-assay accuracy and precision was measured. Natalizumab was spiked in human serum at 2, 8 and 16 ug/mL. The samples were analyzed in 5 independent runs in triplicates (16 ug/mL) or quintuplicates (2-8 ug/mL). Analyte recovery was calculated for each concentration as a measure of accuracy. Recovery was found to be between 80-120% of nominal concentrations, within acceptance criteria (Calibrated value/Nominal Value*100). Intra-assay precision was calculated using the same set of samples. A coefficient of variation (% CV) below 15% was obtained for all concentrations tested (SD/mean*100). The results are presented in Table 4:

TABLE 4

| | Intra-assay Accuracy and Precision | | | | | | | | | | | |
|---|---|---|---|---|---|---|---|---|---|---|---|---|
| Nominal | % recovery | | | | | | | | | | | |
| Concentration | Run 1 | | Run 2 | | Run 3 | | Run 4 | | Run 5 | | Cumulative | |
| (ug/mL) | Mean | SD | Mean | SD | Mean | SD | Mean | SD | Mean | SD | Mean | SD |
| 2 | 101.7 | 6.2 | 108.8 | 5.8 | 111.4 | 5.6 | 113.8 | 4.2 | 121.6 | 6.3 | 93.4 | 7.7 |
| 8 | 90.5 | 6.3 | 99.7 | 5.6 | 113.1 | 9.5 | 99.0 | 3.6 | 82.6 | 2.4 | 97.0 | 4.6 |
| 16 | 96.8 | 8.1 | 92.4 | 5.7 | 87.6 | 7.6 | 90.5 | 1.6 | 99.4 | 15.4 | 111.4 | 5.6 |
| Nominal | % CV | | | | | | | | | | | |
| Concentration | Run 1 | | Run 2 | | Run 3 | | Run 4 | | Run 5 | | Cumulative | |
| (ug/mL) | | | | | | | | | | | | |
| 2 | 5.5 | | 4.8 | | 4.5 | | 3.3 | | 4.7 | | 4.5 | |
| 8 | 6.2 | | 5.1 | | 7.5 | | 3.2 | | 2.2 | | 4.9 | |
| 16 | 6.9 | | 5.1 | | 7.1 | | 1.5 | | 12.6 | | 6.6 | |

Inter-assay accuracy and precision was also measured. Natalizumab was spiked in human serum at 2, 8 and 16 ug/mL. The samples were analyzed in 5 independent runs in triplicates (16 ug/mL) or quintuplicates (2-8 ug/mL). Analyte recovery was calculated for each concentration as a measure of accuracy, and was found to be between 80-120% (Calibrated value/Nominal Value*100). The Coefficient of Variation was calculated for each replicate across all 5 runs. A cumulative % CV for each concentration is shown. (% CV: SD/mean*100). The results are presented in Table 5:

TABLE 5

Inter-assay Accuracy and Precision

| Nominal concentration (ug/mL) | % recovery | | | | | | | | | | |
|---|---|---|---|---|---|---|---|---|---|---|---|
| | Rep 1 | | Rep 2 | | Rep 3 | | Rep 4 | | Rep 5 | | Cumulative |
| | Mean | SD | Mean | SD | Mean | SD | Mean | SD | Mean | SD | Mean | SD |
| 2 | 114.2 | 5.8 | 115.6 | 6.0 | 108.5 | 12.5 | 112.0 | 7.8 | 106.9 | 8.4 | 111.4 | 3.7 |
| 8 | 99.5 | 12.1 | 99.1 | 10.2 | 96.6 | 12.4 | 96.2 | 16.4 | 93.4 | 11.2 | 97.0 | 2.3 |
| 16 | 96.2 | 13.9 | 94.0 | 6.7 | 95.2 | 12.4 | — | | — | | 95.1 | 1.1 |

| Nominal concentration (ug/mL) | % CV | | | | | |
|---|---|---|---|---|---|---|
| | Rep 1 | Rep 2 | Rep 3 | Rep 4 | Rep 5 | Cumulative % CV |
| 2 | 4.5 | 4.6 | 10.3 | 6.2 | 7.0 | 6.5 |
| 8 | 10.9 | 9.2 | 11.4 | 15.2 | 10.7 | 11.5 |
| 16 | 12.9 | 10.3 | 11.7 | — | — | 11.6 |

Figure 15:
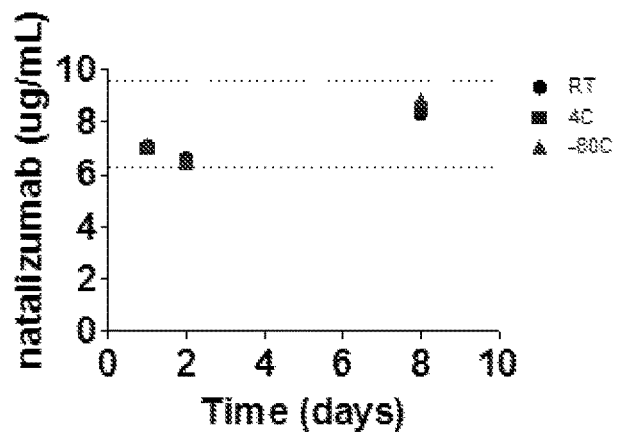
FIG. 15 depicts stability of human serum samples spiked with a natalizumab-specific VERITOPE™ (NTZ-01-Bio; SEQ ID NO:24) up to 8 days.

Spiked serum sample stability of the natalizumab-specific VERITOPE™ (NTZ-01-Bio; SEQ ID NO:24) was measured and the results presented in FIG. 15. Serum samples spiked with 8 ug/mL natalizumab were quantified using the VERITOPE™ ELISA after exposure to different storage conditions to determine sample stability. Exposure to room temperature (RT), 4 C or −80 C for 1, 2 and 8 days did not affect stability.

Figure 16:
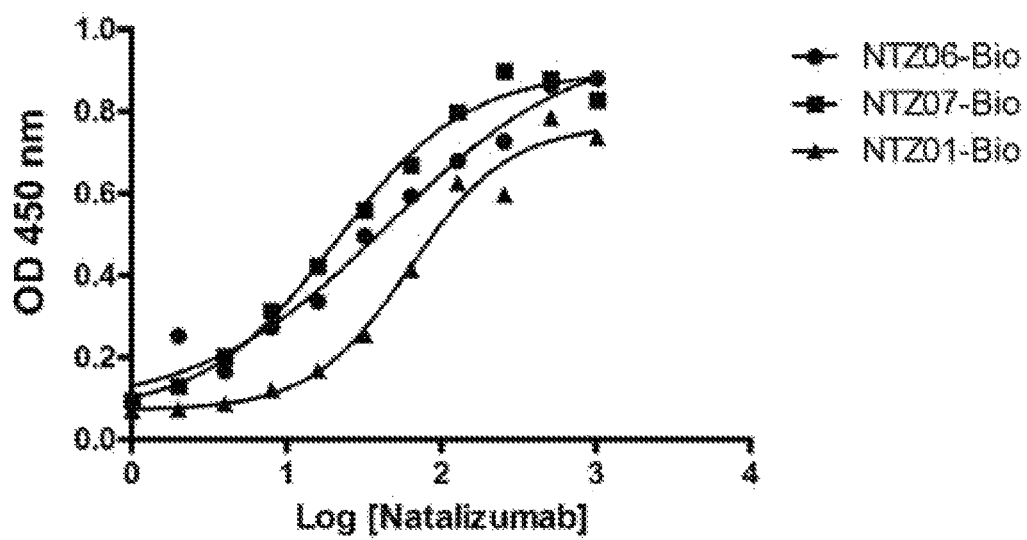
FIG. 16 depicts a comparison of the calibration curves for NTZ01 (SEQ ID NO:24), NTZ06 (SEQ ID NO:29), and NTZ07 (SEQ ID NO:30) natalizumab-specific VERITOPES™.
Figure 17:
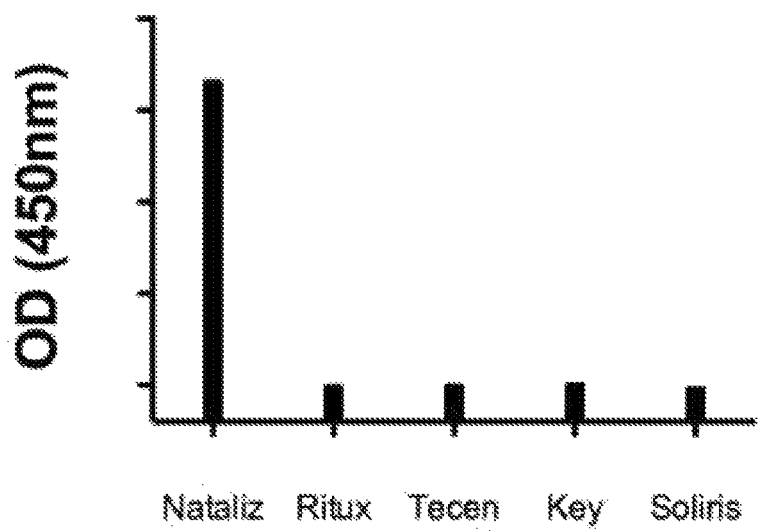
FIG. 17 depicts the specificity of natalizumab-specific VERITOPE™ NTZ07 (SEQ ID NO:30) compared to 4 other monoclonal antibodies.

Example 9: Comparison of First Generation and Second Generation Natalizumab VERITOPES™ ELISA Calibration Curve The sensitivity of different mimetope peptides (NTZ-06-Bio, SEQ ID NO:29; NTZ-07-Bio, SEQ ID NO:30; and NTZ-01-Bio, SEQ ID NO:24) for detection of natalizumab in human serum was determined, and the results are presented in FIG. 16. Experimental conditions used were similar to those described in Example 3, above. The Limit of Blank for NTZ-07-Bio was 85.6+/−41 ng/ml. The selectivity for the natalizumab-specific VERITOPE™ (NTZ-07-Bio; SEQ ID NO:30) for natalizumab over other therapeutic monoclonal antibodies was measured and the results presented in FIG. 17. Human serum was spiked with different therapeutic monoclonal antibodies (Nataliz=natalizumab; Ritux=rituximab; Tecen=atezolizumab; Key=pembrolizumab; Soliris=eculizumab) and binding to natalizumab-specific peptide NTZ-07-Bio (SEQ ID NO:30) was evaluated in ELISA. As shown in FIG. 17, VERITOPE™ selectively captures natalizumab in presence of other circulating human IgG and VERITOPE™ does not capture other mAb drugs.

Results from previous quantitation of select clinical samples with anti-idiotype and a First Generation VERITOPE™ (NTZ-01-Bio; SEQ ID NO:24) were compared with results from quantitation of the same select clinical samples using a new assay with Second Generation VERITOPE™ NTZ-06-Bio (SEQ ID NO:29) and NTZ-07-Bio (SEQ ID NO:30) and the data presented in Table 6:

TABLE 6

Comparison of 1$^{st}$ Generation and 2$^{nd}$ Generation Natalizumab VERITOPES™ Quantitation

| | Previous Assay | | New Assay | | |
|---|---|---|---|---|---|
| Sample # | Anti-Id | NTZ01 | NTZ01 | NTZ06 | NTZ07 |
| 12 | 19.1 | 13.8 | 15.6 | 18.8 | 20.6 |
| 20 | 33.6 | 29.5 | 61.5 | 71.9 | 76.4 |
| 24 | 14.7 | 1.7 | ND | 1.4 | 2 |
| 30 | 10.3 | 2.6 | 2.6 | 3.4 | 4.4 |
| 32 | 46.8 | 35.9 | 47.9 | 62.8 | 68.8 |

Results from previous quantitation of select clinical samples with anti-idiotype and a First Generation VERITOPE™ (NTZ-01-Bio; SEQ ID NO:24) were compared with results from a new assay with a Second Generation VERITOPE™ NTZ-07-Bio (SEQ ID NO:30) and the data presented in Table 7:

TABLE 7

Comparison of Anti-Idiotype, 1$^{st}$ Generation, and 2$^{nd}$ Generation Natalizumab VERITOPES™ Quantitation

| | Previous Assay | | New Assay |
|---|---|---|---|
| Sample # | Anti-Id | NTZ01 | NTZ07 |
| 1 | 28.2 | 11.3 | 18.9 |
| 2 | N/A | 24.9 | 33.4 |
| 3 | 4.0 | 0.0 | 1.0 |
| 4 | 8.2 | 2.1 | 3.0 |

TABLE 7-continued

Comparison of Anti-Idiotype, 1st Generation, and 2nd Generation Natalizumab VERITOPES™ Quantitation

| | Previous Assay | | New Assay |
|---|---|---|---|
| Sample # | Anti-Id | NTZ01 | NTZ07 |
| 5 | 4.0 | 1.1 | 1.1 |
| 9 | 23.7 | 6.2 | 7.7 |
| 10 | 25.0 | 16.6 | 21.6 |
| 11 | 18.1 | 3.1 | 5.3 |
| 12 | 14.2 | 0.0 | 3.7 |
| 13 | 2.3 | 0.0 | 0.8 |
| 16 | 29.3 | 5.7 | 10.7 |
| 17 | 11.5 | 5.6 | 13.1 |
| 19 | 20.5 | 0.9 | 2.8 |
| 22 | 21.4 | 9.6 | 26.1 |
| 23 | 3.5 | 0.0 | 0.4 |
| 24 | 6.7 | 0.6 | 0.8 |
| 25 | 9.1 | 2.7 | 4.9 |
| 26 | 29.3 | 4.1 | 7.0 |
| 27 | 5.4 | 0.2 | 0.4 |
| 34 | 17.4 | 4.6 | 6.3 |
| 37 | 16.2 | 14.0 | 23.8 |
| 39 | 19.5 | 3.5 | 4.9 |
| 47 | 20.3 | 10.0 | 11.4 |
| 59 | 5.9 | 0.2 | 0.7 |

As shown in Table 7, the Second Generation VERITOPE™ NTZ-07-Bio (SEQ ID NO:30) improves sensitivity, and now measurements that were '0' by NTZ-01-Bio (SEQ ID NO:24) (but not by anti-idiotype) give a value.

While preferred embodiments of the present methods, assays, complexes, and assays have been shown and described herein, it will be obvious to those skilled in the art that such embodiments are provided by way of example only. Numerous variations, changes, and substitutions will now occur to those skilled in the art without departing from the methods, assays, complexes, and assays described herein. It should be understood that various alternatives to the embodiments of the methods, assays, complexes, and assays described herein may be employed in practice. It is intended that the following claims define the scope of the methods, assays, complexes, and assays and that methods and structures within the scope of these claims and their equivalents be covered thereby.

What is claimed is:

1. A method of capturing an antibody or a fragment of the antibody in a sample from a subject, wherein the antibody is natalizumab, comprising:
   a) contacting said sample with a peptide consisting of any one of SEQ ID NOs: 1, 2, 4, 13, 16 and 18-23;
   b) allowing binding of the peptide with the antibody or the fragment of the antibody to form an antibody-peptide complex; and
   c) detecting the antibody-peptide complex.

2. The method of claim 1, wherein the antibody is free, circulating natizumab in the sample and not complexed to a protein prior to step a.

3. The method of claim 1, wherein the peptide is attached to a solid support.

4. The method of claim 1, wherein the peptide binds to the antigen binding site of the antibody.

5. The method of claim 1, wherein detecting step c) comprises detection with a detectable label.

6. The method of claim 1, wherein the detecting of the antibody-peptide complex is performed by Western blot analysis, dot blot analysis, flow cytometry, enzyme-linked immunosorbent assay (ELISA), lateral flow immunoassay, radioimmunoassay (RIA), competition immunoassay, dual antibody sandwich assay, chemiluminescent assay, bioluminescent assay, fluorescent assay, or agglutination assay.

7. The method of claim 1, wherein the sample is a biological fluid.

8. The method of claim 1, wherein the subject is a human.

9. The method of claim 7, wherein the biological fluid contains antibody at a concentration of between about 0.5 mcg/mL to 120 mcg/mL.

10. The method of claim 6, wherein the detecting comprises determining the level of the antibody in the sample.

11. The method of claim 10, wherein the sample is from a subject treated with natalizumab, the method further comprising modifying a subject's treatment by adjusting a subject's dose of natalizumab based on the determined level of the antibody in the sample.

12. The method of claim 11, wherein the subject's treatment is for treating progressive multifocal leukoencephalopathy (PML).

* * * * *

SEQUENCE LISTING

```
<160> NUMBER OF SEQ ID NOS: 30

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Cys Pro Met Asn Glu Ser Lys Phe Cys Gly Gly Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Cys Pro Ser Asn Pro Ser Lys Phe Cys Gly Gly Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Cys Asn Trp Met Ile Asn Lys Glu Cys Gly Gly Gly
1               5                   10
```

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Cys Pro Lys Asn Pro Asn Lys Phe Cys Gly Gly Gly
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Cys Val Pro Ser Lys Pro Gly Leu Cys Gly Gly Gly
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Phe Leu Gly Ala Val Ala Lys Gly Ala Ile His Gly Gly Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ala Ser Trp Leu Gly Ser Ser Ser Asn Val Arg Gly Gly Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ala Met Ala Ser Thr Ser Thr Met Leu Gln His Gly Gly Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

His Phe Ile Asn Val Ser Gly Leu Ala Thr Val Phe Gly Gly Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Asp Tyr His Pro Arg Asp His Thr Ala Thr Trp Gly Gly Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Met Ala Met Glu Gln Thr Asn Ala Asp Tyr Gln Gly Gly Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Pro Thr Asn Glu Ser Ser Pro Lys Gly Ser Asn Gly Gly Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Thr Leu Asn His Ser Trp Leu His Thr Phe Ile Gly Gly Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ser Arg Pro Ala Glu Thr Thr Pro Arg Leu Thr Gly Gly Gly
1               5                   10                  15

<210> SEQ ID NO 15
<211> LENGTH: 26
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Pro Phe His Ser Pro Arg Cys Gly Thr Ala Asn Ser Tyr Ser Cys
1               5                   10                  15

Leu His Met Lys Ile Thr Ser Gly Gly Gly
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Tyr Ala Ala Tyr Pro Pro Cys Pro Gln Asn Leu Ser Lys Phe Cys
1               5                   10                  15

Arg His Ser Ser Ser Pro Gly Gly Gly Gly
            20                  25

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Glu Asn Pro Trp Asn Gln Cys Met Lys Gly Thr Phe Lys Arg Cys
1               5                   10                  15

Ser Tyr Pro Arg Ile Ala Asn Gly Gly Gly
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Tyr Pro His Gly Arg Ser Cys Pro Gln Asn Ile Ser Lys Phe Cys
1               5                   10                  15

Phe Asp His Glu Lys Thr Asn Gly Gly Gly
            20                  25

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gly Gly Glu Trp His Arg Cys Met Ser Glu Glu Gly Lys His Cys
1               5                   10                  15
```

Val Asp Ile Gln Phe Ile Arg Gly Gly Gly
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Leu Thr Val Met Thr Cys Pro His Asn Pro Ser Lys Trp Cys
1               5                   10                  15

Ser Pro Leu Pro Ala Ala Val Gly Gly Gly
            20                  25

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Met Ala Ser Ser Ala Thr Cys Thr Lys Pro Asn Ser Tyr Ser Cys
1               5                   10                  15

Leu His Ala Lys Leu Val Pro Gly Gly Gly
            20                  25

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Pro Ser Pro Pro Lys Asn Cys Ser Lys Phe His Ser Ala Leu Cys
1               5                   10                  15

Lys Gly Val Thr Trp Asn Val Gly Gly Gly
            20                  25

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser His Pro Gln Glu Phe Trp Cys Pro Gln Asn Phe Ser Lys Phe Cys
1               5                   10                  15

Ser Arg Ser Tyr Ser Asn Thr Gly Gly Gly
            20                  25

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: N-term Ac
<220> FEATURE:
<221> NAME/KEY: MISC_FEATURE
<222> LOCATION: (2)..(10)
<223> OTHER INFORMATION: Disulfide bridge
<220> FEATURE:
<221> NAME/KEY: MOD_RES
<222> LOCATION: (14)..(14)
<223> OTHER INFORMATION: Biotin-Lys

<400> SEQUENCE: 24

Ala Cys Pro Met Asn Glu Ser Lys Phe Cys Gly Gly Gly Lys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(10)
<223> OTHER INFORMATION: Disulfide bridge
<220> FEATURE:
<221> NAME/KEY: MOD_RES
<222> LOCATION: (14)..(14)
<223> OTHER INFORMATION: Biotin-Lys

<400> SEQUENCE: 25

Ala Cys Pro Ser Asn Pro Ser Lys Phe Cys Gly Gly Gly Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(10)
<223> OTHER INFORMATION: Disulfide bridge
<220> FEATURE:
<221> NAME/KEY: MOD_RES
<222> LOCATION: (14)..(14)
<223> OTHER INFORMATION: Biotin-Lys

<400> SEQUENCE: 26

Ala Cys Pro Lys Asn Pro Asn Lys Phe Cys Gly Gly Gly Lys
1               5                   10

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(16)
<223> OTHER INFORMATION: Disulfide bridge
<220> FEATURE:
<221> NAME/KEY: MOD_RES
<222> LOCATION: (27)..(27)
```

```
<223> OTHER INFORMATION: Biotin-Lys

<400> SEQUENCE: 27

Ala Tyr Pro His Gly Arg Ser Cys Pro Gln Asn Ile Ser Lys Phe Cys
1               5                   10                  15

Phe Asp His Glu Lys Thr Asn Gly Gly Gly Lys
            20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(16)
<223> OTHER INFORMATION: Disulfide bridge
<220> FEATURE:
<221> NAME/KEY: MOD_RES
<222> LOCATION: (27)..(27)
<223> OTHER INFORMATION: Biotin-Lys

<400> SEQUENCE: 28

Ser His Pro Gln Glu Phe Trp Cys Pro Gln Asn Phe Ser Lys Phe Cys
1               5                   10                  15

Ser Arg Ser Tyr Ser Asn Thr Gly Gly Gly Lys
            20                  25

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(10)
<223> OTHER INFORMATION: Disulfide bridge
<220> FEATURE:
<221> NAME/KEY: MOD_RES
<222> LOCATION: (14)..(14)
<223> OTHER INFORMATION: Biotin-Lys

<400> SEQUENCE: 29

Ala Cys Pro Arg Asn Glu Ser Lys Phe Cys Gly Gly Gly Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(10)
<223> OTHER INFORMATION: Disulfide bridge
<220> FEATURE:
<221> NAME/KEY: MOD_RES
<222> LOCATION: (14)..(14)
<223> OTHER INFORMATION: Biotin-Lys

<400> SEQUENCE: 30

Ala Cys Pro Lys Asn Pro Ser Lys Phe Cys Gly Gly Gly Lys
1               5                   10
```